(12) United States Patent
Kastan et al.

(10) Patent No.: US 7,108,992 B2
(45) Date of Patent: Sep. 19, 2006

(54) ATM KINASE COMPOSITIONS AND METHODS

(75) Inventors: Michael B. Kastan, Cordova, TN (US); Christopher Bakkenist, Cordova, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 263 days.

(21) Appl. No.: 10/307,077

(22) Filed: Nov. 27, 2002

(65) Prior Publication Data

US 2003/0077661 A1    Apr. 24, 2003

(51) Int. Cl.
*C07K 16/40* (2006.01)
*G01N 33/573* (2006.01)

(52) U.S. Cl. .................... 435/7.4; 439/975; 530/387.9; 530/388.26; 530/388.9

(58) Field of Classification Search ................ 435/975, 435/7.4, 935; 530/387.9, 388.26, 388.9, 530/389.8
See application file for complete search history.

(56) References Cited

U.S. PATENT DOCUMENTS

| | | | |
|---|---|---|---|
| 2,233,970 | A | 3/1941 | Andersag et al. |
| 4,181,725 | A | 1/1980 | Voorhees et al. |
| 4,260,615 | A | 4/1981 | Raether et al. |
| 4,284,627 | A | 8/1981 | Raether et al. |
| 4,421,920 | A | 12/1983 | Baudouin et al. |
| 4,431,807 | A | 2/1984 | Strube et al. |
| 5,134,168 | A | 7/1992 | Bitonti et al. |
| 5,242,932 | A | 9/1993 | Gandy et al. |
| 5,278,173 | A | 1/1994 | Davis |
| 5,314,894 | A | 5/1994 | Stecher et al. |
| 5,340,803 | A | 8/1994 | Rubin |
| 5,430,039 | A | 7/1995 | Roberts-Lewis et al. |
| 5,596,002 | A | 1/1997 | Hofheinz et al. |
| 5,599,681 | A | 2/1997 | Epstein et al. ............. 435/7.23 |
| 5,624,938 | A | 4/1997 | Pernis |
| 5,635,515 | A | 6/1997 | Chauffert et al. |
| 5,639,761 | A | 6/1997 | Francois et al. |
| 5,668,149 | A | 9/1997 | Oroszlan et al. |
| 5,948,791 | A | 9/1999 | Hofheinz et al. |
| 6,348,311 | B1 | 2/2002 | Kastan et al. ................ 435/5 |
| 6,387,640 | B1 | 5/2002 | Kastan et al. ................ 435/15 |
| 6,417,177 | B1 | 7/2002 | Nelson |
| 6,475,518 | B1 | 11/2002 | Baumgart et al. |
| 6,579,898 | B1 | 6/2003 | Humphrey |
| 6,670,167 | B1 * | 12/2003 | Chen et al. ............ 435/252.33 |
| 6,808,877 | B1 * | 10/2004 | Wang et al. ................ 435/5 |
| 6,916,627 | B1 * | 7/2005 | Kastan et al. ................ 435/7.4 |
| 2002/0044919 | A1 | 4/2002 | Yu |
| 2002/0169140 | A1 | 11/2002 | Prendergast |
| 2003/0157572 | A1 * | 8/2003 | Kastan et al. ................ 435/7.2 |
| 2004/0092583 | A1 | 5/2004 | Prendergast |

FOREIGN PATENT DOCUMENTS

| | | |
|---|---|---|
| WO | WO 98/56391 | 12/1998 |
| WO | WO-01/52868 A1 | 7/2001 |
| WO | WO-02/13826 A1 | 2/2002 |
| WO | WO-03/013535 A2 | 2/2003 |

OTHER PUBLICATIONS

Cruse et al, Illustrated Dictionary of Immunology, CRC Press, Inc., 1995. p. 316.*
Alligood et al., "Ionoclonal Antibodies Generated Against Recombinant ATM Support Kinase Activity", Hybridoma 2000 19(4):317-321.
Banin et al., "Enhanced Phosphorylation of p53 by ATM in Response to DNA Damage", Science 1998 281:1674-1677.
Canman et al., "Activation of the ATM Kinase by Ionizing Radiation and Phosphorylation of p53", Science 1998 281:1677-1679.
Hartwell et al., "Cell Cycle Control and Cancer", Science 1994 266:1821-1828.
Johnson et al., "Active and Inactive Protein Kinases:Structural Basis for Regulation", Cell 1996 85:149-158.
Kastan Michael, "Ataxia-Telangiectasia—Broad Implications for a Rare Disorder", N. Engl. J. Med. 1995 333(10):662-663.
Kastan et al., "The Many Substrates and Functions of ATM", Molecular Cell Biology 2000 1:179-186.
Kim et al., "Substrate Specificities and Identification of Putative Substrates of ATM Kinase Family Members", J. Biol. Chem. 1999 274(53):37538-37543.
Lim et al., "ATM phosphorylates p95/nbs1 in an S-phase checkpoint pathway", Nature 2000 404:613-617.
Morgan et al., "Fragments of ATM Which Have Dominant-Negative or Complementing Activity", Molecular and Cellular Biology 1997 17(4):2020-2029.
Sarkaria et al., "Inhibition of Phosphoinositide 3-Kinase Related Kinases by the Radiosensitizing Agent Wortmannin", Cancer Research 1998 58:4375-4382.
Shiloh et al., "ATM:Genome Stability, Neuronal Development, and Cancer Cross Paths", Advances in Cancer Research 2000 83:209-253.
Burkard et al., "Antiteratogenic and anticarcinogenic effects of X-rays in urethane-treated NMRI mice", Int. J. Radiat. Biol. 1987 51(6):1031-1039.

(Continued)

Primary Examiner—David Saunders
(74) Attorney, Agent, or Firm—DArby & Darby

(57) ABSTRACT

The present invention provides methods for detecting activation of ATM kinase, DNA damage, and DNA damaging agents. Further provided are antibodies which specifically recognize the phosphorylation state of Ataxia Telangiectasia-Mutated (ATM) kinase. Methods of identifying agents which modulate the activation and activity of ATM kinase are also provided.

9 Claims, No Drawings

OTHER PUBLICATIONS

Geser et al., "Effect of a Malaria Suppression Program on the Incidence of African Burkitt's Lymphoma", American Journal of Epidemology 1989 129(4):740-753.

Bielicky and Zák, "The protective effect of chloroquine disphosphate", Strahlentherapie 1967 133(2):307-311 Summary Only Considered.

Angele, S. and Hall, J., The ATM gene and breast cancer: is it really a risk factor? Mutation Res. 462:167-178, 2000.

Al-Herz, A., et al., "Survey of antimalarial use of lupus pregnancy and lactation", J. Rheumatol., 2002, vol. 29; pp. 700-706.

Arnold, A.M., et al., "Interaction of VP16-213 with the DNA repair antagonist chloroquine," Cancer Chemotherapy and Pharmacology, 1982, vol. 7, pp. 123-126.

Azzam, E.I., "Low dose ionizing radiation decreases the frequency of neoplastic transformation to a level below the spontaneous rate in C3h 10T 1/2 cells", Radiation Res., 1996, vol. 146, pp. 369-373.

Bakkenist, C.J., and Kastan, M.B., "DNA damage activates ATM through intermolecular autophosphorylation and dimer dissocation", Nature, 2003, vol. 421, pp. 499-506.

Bartkova, J., et al., "DNA damage response as a candidate anti-cancer barrier in early human tumorigenesis", Nature, 2005, vol. 434, pp. 864-869.

Bartkova, J., et al., "ATM activation in normal human tissues and testicular cancer", Cell Cycle, vol. 4(6), pp. 838-845, 2005.

Bhattarcharjee, D., "Role of radioadaptation on radiation-induced thymic lymphoma in mice", Mutation Res., 1996, vol. 358, pp. 231-235.

Bielicky T., et al., "Effect of chloroquine-diphosphate administration on the skin damage in guinea pigs caused by x-ray irradiation," Journal of Investigative Dermatology, 1966, 47(2), pp. 73-77.

Boniver, J., et al., "Cellular events in radiation-induced lymphomagenesis", Int. J. Radiat. Biol., 1990, vol.57, pp. 693-698.

Briceno, Eduardo, et al., "Therapy of glioblastoma multifome improved by the antimutagenic chloroquine", Neurosurg. Focus, 2003, vol. 14, No. 2, pp. 1-6.

Cadet, J. et al., "Radiation-induced DNA damage: formation, measurement, and biochemical features", Environ Pathol Toxicol Oncol., 2004, vol. 23, pp. 33-43.

Cobreros et al., "Modifiers of radiation action on DNA screened by analytical ultracentrifugation," Radiation Research, 1982, 92(2), pp. 255-267.

Collis, S.J., et al., "Evasion of early cellular response mechanisms following low level radiation-induced DNA damage ", The Journal of Biological Chemistry, Nov. 26, 2004, vol. 279, No. 48, pp. 49624-49632.

Costedoat-Chalumeau, N., et al., "Safety of hydroxchloroquine in pregnant patients with connective tissue diseases", Arthritis Rheumatism, 2003, vol. 48, pp. 3207-3211.

Ducharme, J., et al., "Clinical pharmacokinetics and metabolism of chloroquine. Focus on recent advancements," Clinical Pharmacokinetics, 1996, 31(4), pp. 257-274.

Feinendegen, L.E., et al., "Intracellular stimulation of biochemical control mechanisms", Healthy Physics, 1987, vol. 52, pp. 663-669.

Fernandez, Y., et al., "Effect of systemic lupus erythematosus (SLE) treatment drugs on G1-101A breast tumor cell growth," Life Sciences, 2000, vol. 67, pp. 567-575.

Freeman, R.G., et al., "Skin cancer and the sun," CA Cancer J Clin., 1967, vol. 17, No. 5, pp. 231-239.

Frigerio, N.A., et al., "Carcinogenic and genetic hazard from background radiation. Biological and environmental effects of low-level radiation", IAEA, 1976, vol. II, pp. 385-393.

Haberkorn, A., et al., "Antimalarial activity in animals of the optical isomers of chloroquine diphosphate", Trop Med Parasitol, 1979, vol. 30, pp. 308-312.

Hagihara, H., et al., "Vascular protection by chloroquine during brain tumor therapy with Tf-CRM107," Cancer Research, Jan. 15, 2000, vol. 60, pp. 230-234.

Horejsi, Z., et al., "Distinct functional domains of Nbs1 modulate the timing and magnitude of ATM activation after low doses of ionizing radiation", Oncogene, 2004, vol. 23, pp. 3122-3127.

Ikushima, T., et al., "Radioadaptive response; Efficient repair of radiation induced DNA dmaage in adapted cells", Mutation Res., 1996, vol. 358, pp. 193-198.

Inoue, S. et al., "Antimelanoma activity of chloroquine,an antimalarial agent with high affinity for melanin," Pigment Cell Research, 1993, vol. 6, pp. 354-358.

Kaplan, H.S., et al., "A quantitative dose-response study of lymphoid-tumor development in irradiated C57 black mice", J Natl Cancer inst, 1952, vol. 13, pp. 185-208.

Kastan, M.B., et al., "Multiple signaling pathways involving ATM", Cold Spring Harb Symp Quant Biol, 2000, vol. 65, pp. 521-526.

Kawanishi et al., "Mechanism of guanine-specific DNA damage by oxidative stress and its role in carcinogenesis and aging," Mutation Research, 2001, 488(1), pp. 65-76.

Kim, S.H., et al., "Enhancement of the radiation response of cultured tumor cells by chloroquine," Cancer: A Journal of the American Cancer Society, Sept. 1973, vol. 32, pp. 536-540.

Kitagawa, R., et al., "Phosphorylation of SMC1 is a critical downstream event in the ATM-NBS1-NBS1-BRCA1 pathway", Genes Dev., 2004, 18(12), pp. 1423-1438.

Knox, John M., et al., "Prophylactic Use of Chloroquine to Prevent Skin Cancer", Archives of Dermatology, Mar. 1963, vol. 87, pp. 315-322.

Knox, J.M., et al., "Effect of chloroquine on erythematous and carcinogenic response to ultraviolet light," A.M.A. Archives of Dermatology, Apr. 1960, vol. 81, pp. 122/570-128/576.

Kumatori, T., et al., "Follow up studies over a 25 year period on the Japanese fishermen exposed to radioactive fallout in 1954", pp. 35-54, in Hubner K.F., and Fry, A.A. eds., The medical basis for radiation preparedness, Elsevier, New York, 1980.

Lagneaux, L., et al., "Early induction of apoptosis in B-chronic lymphocytic leukaemia cells by hydroxychloroquine: activation of caspase-3 and no protection by survival factors", British Journal of Haematology, 2001, vol. 112, pp. 344-352.

Lee, J.-H., and Paull, T.T., "Direct activation of the ATM protein kinase by the Mre11/Rad50/Nbs1 complex", Science, 2004, vol. 304, pp. 93-96.

Lieberman, L.M. et al., "Treatment doses of $^{T31}$ 1-labeled chloroquine analog in normal and malignant melanoma dog," Journal of Nuclear Medicine, Jan. 1971, vol. 12, No. 4, pp. 153-159.

Mifune, M., et al., "Cancer mortality survey in a spa area (Misasa, Japan) with a high radon background", Japanese J. Cancer Res., 1992, vol. 83, pp. 1-5.

Mitchel, R.E.J., et al., "The adaptive response modifies latency for radiation-induced myeloid leukemia in CBA/H mice", Radiation Res., 1999, vol. 152, pp. 273-279.

Nambi, K.S.V., Soman, S.D., "Environmental radiation and cancer in India", Health Physics, 1987, vol. 52, pp. 653-657.

Ofori-Adjei, D., et al., "Enantioselective analysis of chloroquine and desethylchloroquine after oral administration of racemic chloroquine", Therap Drug Monitor, 1986, vol. 8, pp. 457-461.

Oikawa et al., "Site-specific DNA damage at the GGG sequence by UVA involves acceleration of telomere shortening, " Biochemistry, 2001, 40, pp. 4763-4768.

Pathak, M.A., "Sunscreens:topical and systemic approaches for protection of human skin against harmful effects of solar radiation," Journal of the American Academy of Dermatology, 1982, 7(3), pp. 285-312.

Pazmino, N.H. et al., "Chloroquine: Nonselective inhibition of recovery from radiation injury in tumors and normal tissues," Radiation Research, 1974, vol. 60, pp. 54-61.

Reyes, S., et al., "Quinacrine enhances carmustine therapy of experimental rat glioma", Neurosurgery, 2001, vol. 49(4), pp. 969-973.

Savitsky, K., et al., "A single ataxia telangiectasia gene with a product similar to Pl-3 kinase", Science, 1995, vol. 268, pp. 1749-1753.

Sjolin-Forsberg et al., "Topical chloroquine applied before irradiation protects against ultraviolet B (UVB)- and UVA-induced erythema but not against immediate pigment darkening, " Photodermatol Photoimmunol Photomed, 1992-93, 9(5), pp. 220-224.

Sotelo, J., et al., "Adding chloroquine to conventional treatment for glioblastome multiforme", Ann. Intern. Med., 2006, vol. 144, pp. 337-343.

Tagoe, C.N., et al., "Effects of chloroquine and its enantiomers on the development of rat embryos in vitro", Teratol., 1995, vol. 52, pp. 137-142.

Tannenberger, S., et al., "[On the value of chloroquine in the treatment of malignant tumor diseases]," Arch Geschwulstforsch, 1967, vol. 29, No. 3., pp. 266-273 (In German).

Unscear, Sources and effects of ionizing radiation, United Nations scientific committee on the effects of atomic radiation, New York, 1994.

Utley, J.F., et al., "Radiosensitization of normal tissue by chloroquine," Radiology, Jul. 1977, vol. 124, pp. 255-257.

Uziel, T., et al., "Requirement of the MRN complex for ATM activation by DNA damage", EMBO, 2003, vol. 22(20), pp. 5612-5621.

Van Duuren, B.L. et al., "Inhibition of tumor induction in two-stage carcinogenesis on mouse skin" Cancer Research, Apr. 1969, vol. 29, pp. 947-952.

Wainer, I.W., et al., "Distribution of enantiomers of hydroxychloroquine and its metabolites in ocular tissues of the rabbit after oral administration of racemic-hydroxycholoroquine", Chirality, 1994, vol. 6, pp. 347-354.

Wei. L., "Epidemiological investigation of radiological effects in high background radiation areas of Yangjiang China", J. Radiation Res., 1990, vol. 31, pp. 119-136.

Wolff, S., "Failla Memorial Lecture. Is radiation all bad? The search for adaptation." Radiation Res., 1992, vol. 131, pp. 117-123.

Wu, X, et al., "ATM phosphorylation of Nijmegen breakage syndrome protein is required in a DNA damage response", Nature, 2000, vol. 405, pp. 477-482.

Yang, Da-Qing, et al., "Participation of ATM in insulin signalling through phosphorylation of eIF-4E-binding protein 1", Nature Cell Biology, Dec. 2000, vol. 2, pp. 893-898.

Yang, J., et al., "ATM and ATR: sensing DNA damage", World J Gastroenterol., 2004, vol. 10, pp. 155-160.

Yang, J., et al., "Protein kinases and their involvement in the cellular responses to genotoxic stress", Mutat. Res., 2003, vol. 543, pp. 31-58.

Yonezawa, M., et al., "Two types of X-ray induced radioresistance in mice, presence of 4 dose ranges with distinct biological effects", Mutation Res., 1996, vol. 358, pp. 237-243.

Zajdela, F. et al., "Inhibition of skin carcinogenesis in vivo by caffeine and other agents," National Cancer Institute Monograph, 1978, pp. 133-140, No. 50.

Zeilhofer, H.U., et al., "Selective growth inhibition of ductal pancreatic adenocarcinoma cells by the lysosomotropic agent chloroquine," Cancer Lett., 1989, 44(1), pp. 61-66.

Zhou, Q., et al., "Control of mammary tumor cell growth in vitro by novel cell differentiation and apoptosis agents," Breast Cancer Research and Treatment, 2002, vol. 75, pp. 107-117.

* cited by examiner

ATM KINASE COMPOSITIONS AND METHODS

This invention was made in the course of research sponsored by the National Institutes of Health (NIH Grant Nos. CA71387). The U.S. government may have certain rights in this invention.

BACKGROUND OF THE INVENTION

Eukaryotic cells have evolved complex mechanisms to deal with environmental stresses. Signal transduction pathways are rapidly activated following exposure to DNA damaging agents and other cellular stresses, and these pathways affect processes such as gene transcription and cell cycle progression (Hartwell and Weinert (1989) *Science* 246:629–634; Hartwell and Kastan (1994) *Science* 266: 1821–1828; Elledge (1996) *Science* 274:1664–1672). The protein encoded by the Ataxia-telangiectasia Mutated (ATM) locus, is a kinase critical for the initiation of signaling pathways following exposure of mammalian cells to ionizing radiation (IR) and to other agents that introduce double-strand breaks into cellular DNA (Kastan and Lim (2000) *Mol. Cell Biol.* 1:179–186; Shiloh and Kastan (2001) *Adv. Cancer Res.* 83:209–254). Cells from Ataxia-telangiectasia (A-T) patients typically lack detectable ATM protein, contain abnormalities in telomere morphology, and exhibit abnormal responses to IR, including increased cell death, increased chromosomal breakage, and cell cycle checkpoint defects (Shiloh (1997) *Ann. Rev. Genet.* 31:635–662). In addition, A-T patients exhibit progressive cerebellar ataxia, immune deficiencies, gonadal atrophy, oculocutaneous telangiectasias, radiation sensitivity, premature aging and increased risk of cancers, particularly lymphomas.

The ATM gene encodes a 370-kDa protein (Accession No. Q13315; SEQ ID NO: 1) that belongs to the phosphoinositide 3-kinase (PI-3K) superfamily (Savitsky, et al. (1995) *Science* 268:1749–1753) which phosphorylates proteins rather than lipids (Banin, et al. (1998) *Science* 281: 1674–1677; Canman, et al. (1998) *Science* 281:1677–1679). The 350 amino acid kinase domain at the C-terminus of this protein is the only segment of ATM with an assigned function. Exposure of cells to IR triggers ATM kinase activity and this function is required for arrests in G1, S, and G2 phases of the cell cycle (Shiloh and Kastan (2001) *Adv. Cancer Res.* 83:209–254). Several substrates of the ATM kinase participate in these IR-induced cell cycle arrests. For example, phosphorylation of p53, mdm2, and Chk2 govern the G1 checkpoint (Banin, et al. (1998) *Science* 281:1674–1677; Canman, et al. (1998) *Science* 281:1677–1679; Maya, et al. (2001) *Genes Dev.* 15:1067–1077; Matsuoka, et al. (2000) *Proc. Natl. Acad. Sci. USA* 97:10389–10394; Chehab, et al. (2000) *Genes Dev.* 14:278–288); Nbs1, Brca1, FancD2, and SMC1 participate in the transient IR-induced S-phase arrest (Lim, et al. (2000) *Nature* 404:613–617; Wu, et al. (2000) *Nature* 405:477–482; Zhou, et al. (2000) *J. Biol. Chem.* 275:10342–10348; Taniguchi, et al. (2002) *Cell* 109:459–472; Kim, et al. (2002) *Genes Dev.* 16:560–570; Yazdi, et al. (2002) *Genes Dev.* 16:571–582; Xu, et al. (2002) *Cancer Res.* 62:4588–4591); and Brca1 and hRad17 have been implicated in the G2/M checkpoint (Xu, et al. (2001) *Mol. Cell. Biol.* 21:3445–3450; Bao, et al. (2001) *Nature* 411:969–974).

The mechanisms by which eukaryotic cells sense DNA strand breaks is unknown, but the rapid induction of ATM kinase activity following IR indicates that it acts at an early stage of signal transduction in mammalian cells (Banin, et al. (1998) *Science* 281:1674–1677; Canman, et al. (1998) *Science* 281:1677–1679). Transfected ATM is a phosphoprotein that incorporates more phosphate after IR treatment of cells (Lim, et al. (2000) *Nature* 404:613–617), suggesting that ATM kinase is itself activated by post-translational modification.

Inhibiting ATM for the treatment of neoplasms, particularly cancers associated with decreased p53 function, has been suggested (Morgan, et al. (1997) *Mol. Cell Biol.* 17:2020–2029; Hartwell and Kastan (1994) *Science* 266: 1821–1828; Kastan (1995) *New Eng. J. Med.* 333:662–663; WO 98/56391). WO 98/56391 further provides genetically manipulated knock-out mice as a model for testing ATM inhibitors and suggests the use of an inhibitory antibody to ATM, a dominant-negative fragment of ATM or an ATM antisense strategy to inhibit ATM.

U.S. Pat. No. 6,387,640 discloses the use of an ATM kinase substrate recognition sequence in an assay system to screen for compounds that modulate ATM-mediated phosphorylation. The substrate recognition sequence provided comprises $Xaa_1$-Xaa-$Xaa_2$-Ser-Gln-Xaa-Xaa (SEQ ID NO: 2) wherein $Xaa_1$ is a hydrophobic amino acid, $Xaa_2$ is a hydrophobic amino acid or aspartic acid, and Xaa is any amino acid.

U.S. Pat. No. 6,348,311 further discloses a method of identifying an inhibitor of ATM-mediated kinase activity by determining the extent of cell survival after HTLV infection.

SUMMARY OF THE INVENTION

One aspect of the present invention provides a method of identifying the activation state of ATM kinase. In a cell, inactive ATM kinase is found as a homodimer or higher order multimer. Upon autophosphorylation of a serine corresponding to residue 1981 of ATM kinase (SEQ ID NO: 1), ATM becomes an active monomer. Accordingly, the method provides determining the phosphorylation state of serine 1981 ($Ser^{1981}$) which is indicative of the activation state of ATM kinase. In a preferred embodiment, monoclonal or polyclonal antibodies which specifically recognize the phosphorylation state of $Ser^{1981}$ are used to determine the phosphorylation state of $Ser^{1981}$ of ATM kinase by immunoassay analysis.

Another aspect of the invention provides a method of detecting DNA damage in a sample comprising identifying the activation state of ATM kinase via the phosphorylation state of $Ser^{1981}$. The method may be used to monitor the effectiveness of radiation therapy or chemotherapy.

Another aspect of the invention provides a method of detecting DNA damaging agents in a biological or environmental sample comprising identifying the activation state of ATM kinase via the phosphorylation state of $Ser^{1981}$. A kit for detecting a DNA damaging agent is also provided.

A further aspect of the invention provides a method of producing soluble ATM kinase by contacting a first polypeptide of ATM kinase containing the kinase domain with a second polypeptide of ATM kinase containing $Ser^{1981}$. The first and second polypeptides may be produced separately or as a single polypeptide in the same cell.

A further aspect of the invention provides a cell-based assay for identifying agents which modulate the activation of ATM kinase. The method provides contacting cells containing ATM kinase with an agent and determining whether said agent agonizes or antagonizes the activation of ATM kinase in the cell. The activation state of ATM kinase is identified via the phosphorylation state of $Ser^{1981}$.

A further aspect of the invention provides a cell-free assay for identifying agents which modulate ATM kinase activity. The method provides contacting soluble ATM kinase protein with an agent and ATP and determining whether said agent agonizes or antagonizes the ATM kinase activity.

These and other aspects of the present invention are set forth in more detail in the following description of the invention.

DETAILED DESCRIPTION OF THE INVENTION

It has now been found that the major site of ATM kinase phosphorylation is located at serine residue 1981 (Ser$^{1981}$) of ATM kinase (SEQ ID NO: 1), also referred to herein as ATM. Phosphorylation of Ser$^{1981}$ results from intermolecular autophosphorylation. The phosphorylation of Ser$^{1981}$ does not directly regulate the activity of the kinase, but instead disrupts ATM kinase oligomers which in turn allows accessibility of substrates to the ATM kinase domain. The rapidity and stoichiometry of the phosphorylation reaction indicate that ATM is not activated by binding directly to DNA strand breaks. While not wishing to be bound by any particular theory, it is believed that DNA damage rapidly causes changes in higher order chromatin structures that initiate this activation.

Not to be held to any one particular mechanism of action, it is believed that in the unperturbed cell, ATM is sequestered as a dimer or higher order multimer with its kinase domain bound to an internal domain of a neighboring ATM molecule containing Ser$^{1981}$. In this complex, ATM is unable to phosphorylate other cellular substrates. Following DNA damage, the kinase domain of one ATM molecule phosphorylates Ser$^{1981}$ of an interacting ATM molecule, and the phosphorylated ATM is then dissociated from the complex and is freed to phosphorylate other substrates in the cell. The kinase dead and non-phosphorylatable mutants of ATM retain endogenous ATM in a complex since they cannot be phosphorylated and released after IR, thus inhibiting cellular ATM activity. This mechanism provides an explanation for the dominant inhibitory property of kinase-inactive ATM.

Several different molecular mechanisms have been identified that regulate the activity of protein kinases. Protein kinases are generally restrained in an inactive state with the acquisition of catalytic activity controlled at multiple levels, ranging from the binding of allosteric factors to changes in the subcellular localization of the enzyme (Huse and Kuriyan (2002) *Cell* 109:275–282). Since all protein kinases catalyze the same reaction, their active conformations tend to be structurally similar. However, different classes of kinases have evolved distinct inactive states and adoption of the catalytic conformation of the enzyme can be impeded in different ways. These include steric hindrance of substrate access to the catalytic domain by an activation loop that is often controlled by phosphorylation (Johnson and Noble (1996) *Cell* 85:149–158); allosteric regulation of the activation loop via, for example, the PSTAIRE helix in the cyclin dependent kinase family (De Bondt, et al. (1993) *Nature* 363:595–602; pseudosubstrate inhibition of both substrate and nucleotide binding as seen in twitchin (Hu, et al. (1994) *Nature* 369:581–584); and intramolecular autoinhibition by N-terminal segments that inhibit catalytic activity, as in the case of the EphB2 receptor kinase (Dodelet, and Pasquale (2000) *Oncogene* 19:5614–5619). The results provided herein indicate a novel mechanism of kinase activation in which the cellular activity of one ATM kinase molecule is impeded by intermolecular association with an internal domain of a partner ATM molecule; access of substrates to the catalytic domain is impeded by this association. This type of regulation is similar to pseudosubstrate inhibition, with the major variations being that the pseudosubstrate is a domain of itself (albeit in trans) and that this partner is not a mimic, but actually becomes a substrate in order to release the inhibition.

Accordingly, the present invention provides compositions and methods for identifying the activation state of ATM kinase by determining the phosphorylation state of Ser$^{1981}$ of ATM kinase. The activation of ATM kinase is indicative of DNA damage; thus, the invention further provides methods for detecting DNA damage and DNA damaging agents. Further provided is a method for producing soluble ATM kinase by combining a first polypeptide of ATM kinase containing the kinase domain with a second polypeptide of ATM kinase containing Ser$^{1981}$. Methods of identifying agents which modulate activation of ATM kinase in a cell and ATM kinase activity are also provided.

One aspect of the invention provides a method of identifying the activation state of ATM kinase in a cell. In an unperturbed cell (i.e., a cell in which no DNA damage has occurred), ATM kinase is found in a dimer or multimer which is the inactivate state wherein ATM is unable to phosphorylate other cellular substrates. Upon DNA damage, ATM autophosphorylates Ser$^{1981}$ and is converted into a monomer which is the active state wherein ATM is able to phosphorylate other cellular substrates. Therefore, in a cell, the active and inactive states (i.e., activation states) of ATM kinase are distinguishable by the phosphorylation state of Ser$^{1981}$ of ATM kinase (SEQ ID NO: 1). As one of skill in the art can appreciate, the activation state of any homolog or mutant of ATM kinase may be identified by determining the phosphorylation state of a serine corresponding to residue 1981 of ATM kinase. The location of the critical serine residue corresponding to Ser$^{1981}$ of ATM kinase can readily be determined by comparing the sequence of ATM kinase (SEQ ID NO: 1) with the sequence of homologs or mutants of ATM kinase.

In general, the method of identifying the activation state of ATM kinase comprises obtaining a sample such as a biopsy sample, tissue, cell or fluid (e.g., whole blood or plasma) isolated from a subject and determining the phosphorylation state of Ser$^{1981}$ of ATM kinase in the sample. Kinase inhibitors may be present during the isolation of ATM kinase to preserve the phosphorylation state of Ser$^{1981}$ as it would have been found in the cell prior to the isolation step. It is contemplated that the phosphorylation state of Ser$^{1981}$ of ATM may be determined using a variety of separation and/or detection methods, including those exemplified herein. For example, [$^{32}$P] phosphorylated ATM is digested with trypsin and separated by well-known conventional column chromatography, 2-D gel electrophoresis, or capillary electrophoresis methodologies. For separation by column chromatography, reverse-phase HPLC may be employed with collection via peak detection. Under the conditions used for reverse-phase HPLC (0.05% TFA, pH 2.2), a phosphorylated peptide generally elutes slightly earlier than the corresponding non-phosphorylated peptide and may or may not be separated from it. Once HPLC fractions containing the Ser$^{1981}$ phosphorylated peptide are located by Cerenkov counting, a small aliquot of each may be analyzed by MALDI-MS.

As an alternative to radiolabelling, western blots made from 2-D gels may be probed using anti-phosphoserine antibodies (Research Diagnostics, Inc., Flanders, N.J.) to recognize the degree of phosphorylation of a peptide fragment containing Ser$^{1981}$.

Alternatively, one may use a phosphoprotein purification kit (QIAGEN®, Valencia, Calif.) for separation of the phosphorylated from the unphosphorylated cellular protein fraction. The affinity chromatography procedure, in which phosphorylated proteins are bound to a column while unphosphorylated proteins are recovered in the flow-through fraction, reduces complexity and greatly facilitates phosphorylation-profile studies. ATM may then be purified from each fraction and the degree of phosphorylation of a peptide fragment containing ser$^{1981}$ determined via autoradiography or immunoassays.

In a preferred embodiment, the phosphorylation stato of Ser$^{1981}$ of ATM kinase is detected using antibodies which specifically recognize the phosphorylation state of Ser$^{1981}$ of ATM kinase (SEQ ID NO:1) Such antibodies may be utilized with or without purification, fragmentation, or fractionation or ATM. An antibody which specifically recognizes the phosphorylation state of Ser$^{1981}$ of ATM kinase (SEQ ID NO:1) comprises polyclonal. antibody αSer$^{1981}$ which specifically recognizes unphosphorylated Ser$^{1981}$; arid polyclonal antibody α-Ser$^{1981}$-P and monoclonal antibodies 7c10, 12E10, 13C5, 13H4, 2H12, 7A4, 9D8 and 10H11, which specifically recognize phosphorylated Ser$^{1981}$. An antibody is said to specifically recognize the phosphorylation state of Ser$^{1981}$ if it is able to discriminate between the unphosphorylated and phosphorylated forms of Ser$^{1981}$ and bind ATM to form an ATM kinase-antibody complex, i.e., antigen-antibody complex. For example, an antibody which specifically recognizes the unphosphorylated state of Ser$^{1981}$ will only bind to an ATM kinase with an unphosphorylated Ser$^{1981}$ arid riot to an ATM kinase with a Phosphorylated Ser$^{1981}$ (e.g., α-Ser$^{1981}$). Likewise, an antibody which specifically recognizes the a phosphorylated Ser$^{1981}$ and not to an ATM kinase with an unphosphorylated Ser$^{1981}$ (e.g., α-Ser$^{1981}$ -P, 7C10, 12E10, 13C5, 13H4, 2H12, 7A4, 9D8, 10H11).

In general, a method of using antibodies which specifically recognize the phosphorylation state of Ser$^{1981}$ in the identification of the activation state of ATM kinase provides contacting a sample with said antibody and detecting the formation of an antigen-antibody complex using an immunoassay. The ATM kinase antigen, as used herein, includes both the phosphorylated and unphosphorylated states of Ser$^{1981}$, however, the phosphorylated state is preferred. The conditions and time required to form the antigen-antibody complex may vary and are dependent on the sample being tested and the method of detection being used. Once non-specific interactions are removed by, for example, washing the sample, the antigen-antibody complex is detected using any one of the well-known immunoassays used to detect and/or quantitate antigens. Exemplary immunoassays which may be used in the methods of the invention include, but are not limited to, enzyme-linked immunosorbent, immunodiffusion, chemiluminescent, immunofluorescent, immunohistochemical, radioimmunoassay, agglutination, complement fixation, immunoelectrophoresis, western blots, mass spectrometry, antibody array, and immunoprecipitation assays and the like which may be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895–904; Harlow and Lane, Antibodies: A Laboratory Manual, Cold Spring Harbor Laboratory, New York (1988) 555–612).

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques (see, for example, Kennedy, et al. (1976) *Clin. Chim. Acta* 70:1–31 and Schurs, et al. (1977) *Clin. Chim Acta* 81:1–40).

In accordance with identifying the activation state of ATM kinase, the presence or absence of the antigen-antibody complex is correlated with active or inactive ATM kinase in a sample, respectively. For example, a sample to which α-Ser$^{1981}$-P binds is indicative of the presence of active ATM kinase in said sample.

As provided herein, monoclonal and rabbit polyclonal antibodies that specifically recognize Ser$^{1981}$, only when it is in either the unphosphorylated (α-Ser$^{1981}$) or phosphorylated (α-Ser$^{1981}$-P, 7C10, 12E10, 13C5, 13H4, 2H12, 7A4, 9D8, 10H11) state were generated. Initial specificity of these antibodies for appropriate peptides was demonstrated by ELISA and by specific recognition and blocking on dot blots. The specificity of the antibodies were confirmed on western blots of immunoprecipitated FLAG®-tagged ATM protein where wild-type and kinase-inactive ATM were recognized by both antisera, but ATM protein with Ser$^{1981}$ mutated to alanine (Ser$^{1981}$→Ala) was not recognized by either antisera. The relative amount of wild-type ATM recognized by the α-Ser$^{1981}$ antisera was reduced several-fold within 30 minutes after exposure of the cells to 10 Gy IR, whereas the relative amount of kinase-inactive ATM that was recognized remained the same. Conversely, the relative amount of wild-type ATM recognized by the α-Ser -$^{1981}$-P antisera was increased several-fold 30 minutes after treatment with 10 Gy IR while recognition of kinase-inactive ATM was unaffected. These results mirror the metabolic labeling results using transfected wild-type ATM and kinase-inactive ATM in 293T cells described above.

Upon exposure to IR and UV, endogenous ATM is phosphorylated at Ser$^{1981}$. Non-transformed, exponentially growing primary human fibroblasts were exposed to either 10 Gy IR or 10 J/m$^2$ UV. The α-Ser$^{1981}$-P antisera did not bind to ATM protein immunoprecipitated from unirradiated cells, but recognized ATM one hour following exposure to IR and five hours following exposure to both IR and UV. The relative amount of Ser$^{1981}$ phosphorylation seen five hours following IR treatment was several-fold higher than that seen following UV. This differential recognition was not due to changes in cell cycle distribution which did not change significantly in the first hour after IR. Moreover, primary fibroblasts arrested in G$_0$ also demonstrate this phosphorylation event following exposure to either IR or UV irradiation.

Antibodies provided in the present disclosure are of the monoclonal and polyclonal type. It is contemplated that such antibodies may be natural or partially or wholly synthetically produced. All fragments or derivatives thereof which maintain the ability to specifically bind to and recognize the phosphorylation state of Ser$^{1981}$ of ATM kinase are also contemplated. The antibodies may be a member of any immunoglobulin class, including any of the classes: IgG, IgM, IgA, IgD, and IgE. Derivatives of the IgG class, however, are preferred in the present invention.

ATM kinase antibody fragments may be any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. The antibody fragment may be produced by any means. For instance, the antibody fragment may be enzymatically or chemically produced by fragmentation of an intact antibody or it may be recombinantly produced from a gene encoding the partial antibody sequence. The antibody fragment may optionally be a single-chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. As used herein, an antibody also includes bispecific and chimeric antibodies.

Naturally produced antibodies may be generated using well-known methods (see, e.g., Kohler and Milstein (1975) Nature 256:495–497; Harlow and Lane, In: Antibodies: A Laboratory Manual, Cold Spring Harbor Laboratory, New York (1988)). Alternatively, ATM kinase antibodies which specifically recognize the phosphorylation state of Ser$^{1981}$ of ATM kinase are derived by a phage display method. Methods of producing phage display antibodies are well-known in the art (e.g., Huse, et al. (1989) *Science* 246(4935): 1275–81).

Selection of ATM kinase-specific antibodies is based on binding affinity to ATM kinase which is either phosphorylated or unphosphorylated at Ser$^{1981}$ and may be determined by the various well-known immunoassays indicated above.

Another aspect of the present invention provides a method of detecting DNA damage in a cell by identifying the activation state of ATM kinase. It has now been shown that DNA damaging agents which introduce breaks in the phosphodiester backbone of DNA induce rapid, detectable phosphorylation of Ser$^{1981}$ and hence activation of ATM kinase. Ser$^{1981}$ phosphorylation was examined in exponentially growing primary fibroblasts one and five hours after treatment with IR, thymidine block, the ribonucleotide reductase inhibitor hydroxyurea (HU), the topoisomerase inhibitors camptothecin and etoposide, the DNA alkylating agent methylmethanesulfonate (MMS), the DNA polymerase α inhibitor aphidicolin, or the oxidizing agent H$_2$O$_2$. Phosphorylation of Ser$^{1981}$ in ATM was detected one hour following exposure to 10 Gy IR, 2 nM camptothecin, 17 nM etoposide or 0.1% H$_2$O$_2$, all of which are DNA damaging agents. The only significant change in this pattern five hours after each of these treatments was more prominent phosphorylation following exposure to the alkylating agent, MMS. The delayed Ser$^{1981}$ phosphorylation after MMS was similar to that observed following UV irradiation, an agent which, like MMS, damages DNA bases, but can induce DNA strand breaks either through repair processes or by DNA replication past DNA adducts. Little or no phosphorylation of ATM was apparent over this time frame following exposure to the DNA synthesis inhibitors hydroxyurea, thymidine, or aphidicolin, none of which directly damage DNA. Thus, all agents tested that directly damage DNA by, for example, inducing DNA strand breaks, induced rapid phosphorylation of Ser$^{1981}$, whereas treatments that primarily inhibit DNA synthesis failed to do so.

The kinetics, dose responsiveness and stoichiometry of ATM autophosphorylation following IR were also examined in primary fibroblasts. Over a 24-hour time frame, phosphorylation of Ser$^{1981}$ was maximal by 15 minutes after exposure to 2 Gy IR and remained stable and detectable for at least 24 hours thereafter. Moreover, phosphorylation of Ser$^{1981}$ was detected immediately upon cellular harvesting following the 30 second exposure required to deliver 0.5 Gy IR and was maximal by five minutes. Initial dose responsiveness was evaluated over a range from 1 to 9 Gy, but induction was already maximal at 1 Gy at the 30 minute time point used. A more detailed evaluation of doses less than 1 Gy provided that phosphorylation of Ser$^{1981}$ was detectable following 0.11 Gy and was already maximal following 0.44 Gy at a 15 minute time point.

As the phosphorylation of Ser$^{1981}$ in ATM can be detected following exposure to doses of IR as low as 0.11 Gy, which theoretically should cause just four double-strand breaks in the genomic DNA of a human diploid cell (Rogakou, et al. (1998) *J. Biol. Chem.* 273:5858–5868), the minimal number of DNA double-strand breaks that would induce detectable ATM phosphorylation was determined. SV-40-transformed fibroblasts were obtained that had been stably transfected with a plasmid containing a sequence that can be cut by the restriction enzyme I-SceI, a site which has not been found in any mammalian genome (Richardson, et al. (1999) *Methods Mol. Biol.* 113:453–463). Southern blotting demonstrated that the genome of this cell line contained two copies of the I-SceI site. The (α-Ser$^{1981}$-P antibody was able to detect Ser$^{1981}$ phosphorylation of FLAG®-tagged, wild-type ATM that was co-transfected with I-SceI. No phosphorylation was seen in control transfectants where no active I-SceI was introduced or when either kinase-inactive ATM or ATM mutated at Ser$^{1981}$ was utilized. Therefore, the α-Ser$^{1981}$-P antibody can detect the introduction of as few as two DNA double-strand breaks in cells.

To estimate the fraction of cellular ATM protein that becomes phosphorylated after DNA damage, sequential immunoprecipitations of ATM from irradiated primary fibroblasts were performed with a conventional anti-ATM antibody and with the α-Ser$^{1981}$-P antisera. In the absence of insult, the conventional anti-ATM antibody was able to immunoprecipitate virtually all of the ATM in the first absorption from unirradiated cells, while the α-Ser$^{1981}$-P antisera brought down almost no ATM. The little ATM that was immunoprecipitated by the α-Ser$^{1981}$-P antisera was not recognized by this antibody on western blots, likely due to a very small amount of non-phospho-specific antisera in the polyclonal antibody preparation. Following exposure to 0.5 Gy IR, the amount of ATM immunoprecipitated by the α-Ser$^{1981}$-P antisera in the first absorption was similar to the amount of ATM immunoprecipitated by the conventional anti-ATM antibody and was greater than the remaining cellular ATM that was brought down in the second absorption by the conventional anti-ATM antibody. Since the conventional anti-ATM antibody was not completely efficient in bringing down all of the cellular ATM with a single immunoprecipitation from the irradiated cells it was estimated that at least 50% of the total ATM in an exponentially growing culture of primary human fibroblasts is autophosphorylated on Ser$^{1981}$ by 15 minutes after exposure to 0.5 Gy IR.

Since such a high fraction of cellular ATM becomes phosphorylated so rapidly in the presence of so few DNA strand breaks, it is unlikely that the ATM oligomers could require direct binding to DNA strand breaks for activation and autophosphorylation. Therefore, the introduction of DNA strand breaks may cause a change in the nucleus that activates ATM at a distance from the break itself. As DNA strand breaks introduced by ionizing irradiation rapidly alter topological constraints on DNA (Roti Roti and Wright (1987) *Cytometry* 8:461–467; Jaberaboansari, et al. (1988) *Radiat. Res.* 114:94–104; Malyapa, et al. (1996) *Int. J. Radiat. Oncol. Biol. Phys.* 35:963–973), alterations in some aspect of chromatin structure fit the criteria of being a rapid change and being able to act a distance in the nucleus. Chromatin and chromosome structures can be altered by hypotonic conditions (Earnshaw, and Laemmli (1983) *J. Cell Biol.* 96:84–93; Jeppesen, et al. (1992) *Chromosoma* 101:322–332), therefore ATM phosphorylation following brief exposures of cells to mildly hypotonic buffers was examined. This minimally invasive treatment of cells induced rapid and diffuse phosphorylation of ATM protein as assessed by immunoblot and immunofluorescence. No phosphorylation of histone H2AXγ was observed, therefore there was no evidence for the introduction of DNA strand breaks with this treatment. In contrast, phosphorylation of both ATM and H2AXγ were apparent following IR. The patterns of immunofluorescent staining for ATM following that at the earliest time points, the staining was diffuse across the nucleus, but after several minutes, some foci were seen in addition to the diffuse nuclear staining. This pattern is consistent with a diffuse activation of ATM and migration of a fraction of ATM protein to the sites of DNA strand breaks to phosphorylate substrates at the breaks.

Accordingly, in another preferred embodiment DNA damage in a sample is detected by identifying the activation state of ATM kinase. The method provides obtaining a sample from a subject and determining the phosphorylation state of $Ser^{1981}$ of ATM kinase. The phosphorylation state of $Ser^{1981}$ of ATM kinase may be determined using any one of the techniques provided herein, however, it is preferred that antibodies which specifically recognize the phosphorylation state of $Ser^{1981}$ of ATM kinase be used. A sample containing a phosphorylated $Ser^{1981}$ of ATM kinase, as determined by, for example, the binding of α-$Ser^{1981}$-P antibody, is indicative of active ATM kinase and hence DNA damage in the subject from which the sample was obtained. Accordingly, a method of detecting DNA damage may be used as part of a screen in subjects suspected of having been exposed to a DNA damaging agent. Moreover, the detection method of the invention may be used alone or in combination with other well-known diagnostic methods to confirm DNA damage.

Damage to DNA may have a genetic- or age-related basis or may result from exposure to agents including those which generate DNA adducts by alkylation (e.g., methylmethane sulfonate (MMS), ethylmethane sulfonate (EMS), N-methyl-N-nitro-N-nitrosoguanine (MNNG), dimethylnitrosamine (DMN), dimethyl sulfate), and form intra- and inter-strand crosslinks (e.g., mitomycin C, psoralens). Furthermore, exposure to base analogs, such as bromouracil and aminopurine; nitrous acid; large molecules which bind to bases in DNA and cause them to be noncoding, i.e., "bulky" lesions; chemicals causing DNA strand breaks (e.g., peroxides); and radiation such as ultraviolet and ionizing radiation (e.g., X- and gamma-rays) also result in DNA damage.

Detection of DNA damage in a cell as determined by the activation state of ATM kinase is also useful for monitoring therapeutic effects during clinical trials and other treatment. Thus, the therapeutic effectiveness of an agent, such as a radionucleide for radiation therapy or a cytotoxic agent for chemotherapy designed to cause DNA damage in a cell, can be monitored using the phosphorylation state of $Ser^{1981}$ of ATM kinase, i.e., active ATM kinase, as an end-point target.

A further aspect of the invention provides a method of detecting a DNA damaging agent in a sample. A sample may be either of biological or environmental origin. Biological samples include those provided above as well as food products and ingredients such as dairy items, vegetables, meat and meat by-products, and waste. Environmental samples include environmental material such as surface matter, soil, water, wastewater, sewage, sludge, industrial samples (e.g., industrial water), as well as samples obtained from food and dairy processing instruments, apparatus, equipment, disposable and non-disposable items. In addition to these environmental samples, it is contemplated that drinking water may be used with the method of the present invention. It is intended that the term drinking water encompass all types of water used for consumption by humans and other animals, including but not limited to well water, run-off water, water stored in reservoirs, rivers, streams, etc. The method provides contacting a test cell, which can be of prokaryotic or eukaryotic origin, containing ATM kinase, with a sample suspected of having a DNA damaging agent, allowing the test cell to incubate in the presence of the sample, and detecting whether DNA damage has occurred in the test cell by identifying the activation state of ATM kinase in said cell. Methods for identifying the activation state of ATM kinase in a cell are provided herein. In a preferred embodiment, active ATM kinase, in a cell exposed to a DNA damaging agent, is identified by determining the phosphorylation state of $Ser^{1981}$ using antibodies which specifically recognize the phosphorylation state of $Ser^{1981}$ of ATM kinase.

A further aspect of the invention provides a kit to detect a DNA damaging agent in a sample. The kit comprises antibodies which specifically recognize the phosphorylation state of $Ser^{1981}$ of ATM kinase and are preferably labeled. The kit may further comprise a test cell containing ATM kinase. Further provided in the kit may be a means for determining the antigen-antibody complex using, for example, an immunoassay, and means for comparing the amount of antigen-antibody complex with a standard. The kit may be packaged in a suitable container and further comprise instructions for using the kit to detect DNA damaging agents.

A further aspect of the invention provides a method of producing soluble ATM kinase by contacting the kinase domain of ATM with a fragment of ATM kinase containing $Ser^{1981}$. The domain of ATM containing $Ser^{1981}$ was found to stably interact with the kinase domain of ATM. A GST fusion protein containing residues 1961–2046 of ATM (GST-ATM$^{1961-2046}$) was co-expressed in *E. coli* with a 6×-Histidine (6×-His) fusion protein containing the C-terminal kinase domain of ATM, residues 2712–3056. Although the kinase domain was insoluble in bacteria when co-transfected with GST alone or a GST fusion with the ATM target peptide p53 (residues 1-101), a significant percentage was stabilized and solubilized in the presence of the GST-ATM$^{1961-2046}$ fusion protein. The kinase domain was also solubilized in the presence of the GST-ATM$^{1961-2046}$ fusion protein containing $Ser^{1981}$→Ala, but remained insoluble in the presence of phosphorylation-mimic fusion peptides, $Ser^{1981}$→Asp and $Ser^{1981}$→Glu. Furthermore, the soluble kinase domain co-purified on glutathione-agarose with the GST-ATM$^{1961-2046}$ fusion proteins containing wild-type sequence or Ser$^{1981}$→Ala. These results indicate that the kinase domain and phosphorylation domain can stably bind to one another and that sequences flanking Ser$^{1981}$ are critical for this interaction. The interaction was prevented by mutation of Ser$^{1981}$ to either aspartic acid (Asp) or glutamic acid (Glu), both of which have charged side chains that mimic serine phosphorylation, indicating that phosphorylation of Ser$^{1981}$ may prevent interaction of this domain with the kinase domain.

Diploid human fibroblasts were exposed to a range of formaldehyde concentrations to covalently crosslink endogenous ATM into a minimal complex. A prominent complex containing ATM was immunoprecipitated from cells following treatment of cells with 0.5 mM or 1.0 mM formaldehyde for 10 minutes. This complex migrated electrophoretically considerably slower than the denatured ATM monomer, which runs at 370-kDa, and beyond the range of conventional molecular weight markers. Furthermore, this ATM-containing complex disappeared after exposure of the cells to 10 Gy IR.

The number of ATM molecules present in the complex as well as the dependence of Ser$^{1981}$ phosphorylation on the dissociation of the complex was determined. Hemagglutinin-tagged (HA-tagged) ATM was transfected into 293T cells along with wild-type, kinase-inactive, or Ser$^{1981}$→Ala FLAG®-tagged ATM. In the absence of formaldehyde crosslinking, HA-tagged ATM was immunoprecipitated by anti-FLAG® Sepharose in association with each of the three FLAG®-tagged ATM proteins. Following 2 Gy IR, HA-tagged ATM was immunoprecipitated with both kinase-inactive and Ser$^{1981}$→Ala FLAG®-tagged ATM, but was no longer bound to wild-type FLAG®-tagged ATM. In the absence of irradiation, the relative amounts of kinase-inactive and Ser$^{1981}$→Ala FLAG®-tagged ATM that co-immunoprecipitated with HA-tagged ATM were lower than that of wild-type FLAG®-tagged ATM. This indicated that the association of wild-type, FLAG®-tagged ATM with wild-type, HA-tagged ATM was more stable than that of the mutant, FLAG®-tagged ATMs with HA-tagged ATM. Therefore, ATM exists as a dimer or higher order multimer in unperturbed cells and that intermolecular ATM autophosphorylation on Ser$^{1981}$ is required for the dissociation of the complex following DNA damage.

As the ATM kinase domain interacts stably with the domain containing the autophosphorylation site, it was determined whether a truncated recombinant ATM molecule that included the phosphorylation and kinase domains would fold properly and have kinase activity. A galactose-inducible pYES plasmid containing 6x-His-FLAG®-tagged ATM$^{1923-3056}$ was transfected into *Saccharomyces cerevisiae* and a soluble ATM fragment was recovered. The polypeptide was purified by anti-FLAG® affinity chromatography. Following elution with synthetic FLAG® peptide and subsequent size-exclusion chromatography, the highly purified ATM fragment had kinase activity, exhibited wortmannin-sensitive phosphorylation of a p53 target peptide and autophosphorylation of Ser$^{1981}$. Some of this ATM fragment migrated at the size of a dimer even under the harsh denaturing conditions of the SDS-PAGE gel indicating that the ATM protein homodimerizes in cells.

Accordingly, in another embodiment of the invention, soluble ATM kinase is produced by contacting a first polypeptide comprising the kinase domain of ATM with a second polypeptide comprising a fragment of ATM kinase containing Ser$^{1981}$. The first and second polypeptide may be produced separately or produced as a single polypeptide.

When produced separately, the first polypeptide containing the kinase domain may comprise the entire ATM kinase (i.e., full-length ATM kinase; residues 1–3056 of SEQ ID NO: 1) or a kinase domain fragment which retains the activity of ATM kinase (e.g., residues 2712–3056 of SEQ ID NO: 1). Furthermore, the second polypeptide containing Ser$^{1981}$ may comprise a polypeptide of 50, 75, 85, or 95 amino acid residues with Ser$^{1981}$ located approximately in the center of the polypeptide. An exemplary second polypeptide comprises residues 1961–2046 of SEQ ID NO: 1. When produced as a single polypeptide, the nucleic acid sequences encoding the first and second polypeptide reside on a single contiguous nucleic acid molecule, i.e., translated from one messenger RNA. A single polypeptide may comprise, for example, residues 1923–3056 or 1961–3056 of SEQ ID NO: 1. Alternatively, the single polypeptide may have the first and second polypeptide separated by a linker peptide ranging from 1 to 1000 amino acid residues (e.g., Gly-Ser-Gly, (Gly)$_3$, and the like).

When produced separately, the first and second polypeptide may be expressed from the same or separate expression vectors, from the same or different promoters, in the same or separate cells and combined for purification. Preferably the first and second polypeptide are expressed in the same cell.

Whether produced as a single polypeptide or as separate first and second polypeptides, the soluble ATM kinase will be referred to hereinafter as the ATM kinase polypeptide or simply ATM kinase in the context of producing soluble ATM kinase. Methods of producing ATM kinase in vivo (i.e., cell-based) are provided, however, as will be appreciated by one of skill in the art, ATM kinase may be produced using well-known in vitro transcription and translation methods.

Nucleic acids encoding ATM kinase may be incorporated into a recombinant expression vector in a form suitable for expression of the proteins in a host cell. A suitable form for expression provides that the recombinant expression vector includes one or more regulatory sequences operatively-linked to the nucleic acids encoding ATM kinase in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). It should be understood that the design of the expression vector may depend on such factors as the choice of the host cell to be transfected and/or the level of expression required.

The soluble ATM kinase of the invention may be expressed not only directly, but also as a fusion protein with a heterologous polypeptide, i.e. a signal sequence for secretion and/or other polypeptide which will aid in the purification of ATM kinase. Preferably, the heterologous polypeptide has a specific cleavage site to remove the heterologous polypeptide from ATM kinase.

In general, a signal sequence may be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders may be used. For yeast secretion, one may use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal may be used.

Other useful heterologous polypeptides which may be fused to ATM kinase include those which increase expression or solubility of the fusion protein or aid in the purification of the fusion protein by acting as a ligand in affinity purification. Typical fusion expression vectors include those exemplified herein as well as pGEX (Amersham Pharmacia Biotech, Uppsala, Sweden; Smith, and Johnson (1988) *Gene* 67:31–40), pMAL (New England Biolabs, Beverly, Mass.) and pRIT5 (Pharmacia, Piscataway, N.J.) which fuse GST, maltose E binding protein, or protein A, respectively, to the target recombinant protein.

Eukaryotic microbes such as yeast may be transformed with suitable vectors containing nucleic acids encoding ATM kinase. *Saccharomyces cerevisiae* is the most commonly studied lower eukaryotic host microorganism, although a number of other species are commonly available. Yeast vectors may contain an origin of replication from the 2 micron yeast plasmid or an autonomously replicating sequence (ARS), a promoter, nucleic acid sequences encoding ATM kinase, sequences for polyadenylation and transcription termination, and nucleic acid sequences encoding a selectable marker. Exemplary plasmids include YRp7 (Stinchcomb, et al. (1979) *Nature* 282:39; Kingsman, et al. (1979) *Gene* 7:141; Tschemper, et al. (1980) *Gene* 10:157), pYepSec1 (Baldari, et al. (1987) *EMBO J.* 6:229–234), pMFa (Kurjan and Herskowitz (1982) *Cell* 30:933–943), pJRY88 (Schultz, et al. (1987) *Gene* 54:113–123), and pYES2 (INVITROGEN™ Corporation, San Diego, Calif.). These plasmids contain genes such as trp1, which provides a selectable marker for a mutant strain of yeast lacking the ability to grow in the presence of tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable sequences for promoting ATM kinase expression in yeast vectors include the promoters for metallothionein, 3-phosphoglycerate kinase (Hitzeman, et al. (1980) *J. Biol. Chem.* 255:2073) or other glycolytic enzymes (Hess, et al. (1968) *J. Adv. Enzyme Reg.* 7:149; Holland, et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further disclosed in EP 73,657.

In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and trans-acting elements required for plant transformation. Exemplary vectors include the pMLJ1 shuttle vector (DeBlock, et al. (1984) *EMBO J.* 3:1681–1689) and the non-oncogenic Ti plasmid pGV2850 (Zambryski, et al. (1983) *EMBO J.* 2:2143–2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) *Nucl. Acids Res.* 12:8711–8721) and the non-oncogenic Ti plasmid pAL4404 (Hoekema, et al. (1983) *Nature* 303:179–180).

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV).

In mammalian cells the recombinant expression vector may be a plasmid. Alternatively, a recombinant expression vector may be a virus, or a portion thereof, which allows for expression of a nucleic acid introduced into the viral nucleic acid. For example, replication-defective retroviruses, adenoviruses and adeno-associated viruses may be used. Protocols for producing recombinant retroviruses and for infecting cells in vitro or in vivo with such viruses may be found in Current Protocols in Molecular Biology, Ausubel, F. M. et al. (eds.) Greene Publishing Associates, (1989), Sections 9.10–9.14 and other standard laboratory manuals. Examples of suitable retroviruses include, but are not limited to, pLJ, pZIP, pWE and pEM which are well-known to those skilled in the art. Examples of suitable packaging virus lines include, but are not limited to, ψCrip, ψCre, ψ2 and ψAm. The genome of adenovirus may be manipulated such that it encodes and expresses ATM kinase but is inactivated in terms of its ability to replicate in a normal lytic viral life cycle (Berkner, et al. (1988) *BioTechniques* 6:616; Rosenfeld, et al. (1991) *Science* 252:431–434; Rosenfeld, et al. (1992) *Cell* 68:143–155). Suitable adenoviral vectors derived from the adenovirus strain Ad type 5 dl324 or other strains of adenovirus (e.g., Ad2, Ad3, Ad7 etc.) are well-known to those skilled in the art. Alternatively, an adeno-associated virus vector such as that taught by Tratschin, et al. ((1985) *Mol. Cell. Biol.* 5:3251–3260) may be used to express ATM kinase.

In mammalian expression systems, the regulatory sequences are often provided by the viral genome. Commonly used promoters are derived from polyoma, Adenovirus 2, cytomegalovirus and Simian Virus 40. For example, the human cytomegalovirus IE promoter (Boshart, et al. (1985) *Cell* 41:521–530), HSV-Tk promoter (McKnight, et al. (1984) *Cell* 37:253–262) and β-actin promoter (Ng, et al. (1985) *Mol. Cell. Biol.* 5:2720–2732) may be useful in the expression of ATM kinase in mammalian cells. Alternatively, the regulatory sequences of the recombinant expression vector may direct expression of ATM kinase preferentially in a particular cell type, i.e., tissue-specific regulatory elements can be used. Examples of tissue-specific promoters which may be used include, but are not limited to, the albumin promoter (liver-specific; Pinkert, et al. (1987) *Genes Dev.* 1:268–277), lymphoid-specific promoters (Calame and Eaton (1988) *Adv. Immunol.* 43:235–275), promoters of T cell receptors (Winoto and Baltimore (1989) *EMBO J.* 8:729–733) and immunoglobulins (Banerji, et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci USA* 86:5473–5477), pancreas-specific promoters (Edlund, et al. (1985) *Science* 230:912–916), and mammary gland-specific promoters (e.g., milk whey promoter; U.S. Pat. No. 4,873,316; EP 264,166). Developmentally-regulated promoters are also encompassed, for example the murine hox promoters (Kessel and Gruss (1990) *Science* 249:374–379) and the α-fetoprotein promoter (Camper and Tilghman (1989) *Genes Dev.* 3:537–546).

When the host cell is from an insect (e.g., *Spodoptera frugiperda* cells), expression vectors such as the baculovirus expression vector (e.g., vectors derived from *Autographa californica* MNPV, *Trichoplusia ni* MNPV, *Rachiplusia ou*

MNPV, or *Galleria ou* MNPV, as described in U.S. Pat. Nos. 4,745,051 and 4,879,236) may be employed to express ATM kinase. In general, a baculovirus expression vector comprises a baculovirus genome containing nucleic acid sequences encoding ATM kinase inserted into the polyhedrin gene at a position ranging from the polyhedrin transcriptional start signal to the ATG start site and under the transcriptional control of a baculovirus polyhedrin promoter.

*Escherichia coli* is the most common prokaryotic expression system. Exemplary *E. coli* strains include W3110 (ATCC 27325), *E. coli* B, *E. coli* X1776 (ATCC 31537), and *E. coli* 294 (ATCC 31446). *E. coli* is typically transformed using pBR322 (Bolivar, et al. (1977) *Gene* 2:95) and derivatives thereof.

Promoters most commonly used in recombinant prokaryotic expression vectors include the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP 36,776) the tac promoter (De Boer, et al. (1983) *Proc. Natl. Acad. Sci. USA* 80:21) and pL of bacteriophage 1. These promoters and Shine-Dalgarno sequence may be used for efficient expression of ATM kinase in prokaryotes.

ATM kinase is expressed in a cell by introducing nucleic acid sequences encoding ATM kinase into a host cell, wherein the nucleic acids are in a form suitable for expression of ATM kinase in the host cell. Alternatively, nucleic acid sequences encoding ATM kinase which are operatively-linked to regulatory sequences (e.g., promoter sequences) but without additional vector sequences may be introduced into a host cell. As used herein, a host cell is intended to include any prokaryotic or eukaryotic cell or cell line so long as the cell or cell line is not incompatible with the protein to be expressed, the selection system chosen or the fermentation system employed. Exemplary examples of mammalian cell lines include, but are not limited to, those exemplified herein as well as CHO dhfr-cells (Urlaub and Chasin (1980) *Proc. Natl. Acad. Sci. USA* 77:4216–4220), 293 cells (Graham, et al. (1977) *J. Gen. Virol.* 36:59) or myeloma cells like SP2 or NSO (Galfre and Milstein (1981) *Meth. Enzymol.* 73(B):3–46).

Soluble ATM kinase may be produced in by a variety of non-mammalian eukaryotic cells as well, including insect (e.g,. *Spodoptera frugiperda*), yeast (e.g., *S. cerevisiae, Schizosaccharomyces pombe, Pichia pastoris, Kluveromyces lactis, Hansenula Polymorpha* and *Candida albicans*, and fungal cells (*Neurospora crassa, Aspergillus nidulins, Aspergillus fumigatus*).

Nucleic acid sequences encoding ATM kinase may be introduced into a host cell by standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, *Agrobacterium*-mediated transformation, cell fusion, and ballistic bombardment. Suitable methods for transforming host cells may be found in Sambrook, et al. (Molecular Cloning: A Laboratory Manual, 2nd Edition, Cold Spring Harbor Laboratory press (1989)) and other laboratory manuals.

The number of host cells transformed with a nucleic acid sequence encoding ATM kinase will depend, at least in part, upon the type of recombinant expression vector used and the type of transformation technique used. Nucleic acids may be introduced into a host cell transiently, or more typically, for long-term expression of ATM kinase, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acids of interest. Preferred selectable markers include those which confer resistance to certain drugs, such as G418 and hygromycin. Selectable markers may be introduced on a separate plasmid from the nucleic acids of interest or introduced on the same plasmid. Host cells transfected with nucleic acid sequences encoding ATM kinase (e.g., a recombinant expression vector) and a gene for a selectable marker may be identified by selecting for cells using the selectable marker. For example, if the selectable marker encodes a gene conferring neomycin resistance, host cells which have taken up nucleic acid may be selected with G418 resistance. Cells that have incorporated the selectable marker gene will survive, while the other cells die.

A host cell transformed with nucleic acid sequences encoding ATM kinase may be further transformed with one or more nucleic acids which serve as the target for ATM kinase.

Nucleic acid sequences encoding ATM kinase may be introduced into cells growing in culture in vitro by conventional transformation techniques (e.g., calcium phosphate precipitation, DEAE-dextran transfection, electroporation, etc.). Nucleic acids may also be transferred into cells in vivo, for example by application of a delivery mechanism suitable for introduction of nucleic acid into cells in vivo, such as retroviral vectors (see e.g., Ferry, et al. (1991) *Proc. Natl. Acad. Sci. USA* 88:8377–8381; Kay, et al. (1992) *Hum. Gene Ther.* 3:641–647), adenoviral vectors (see e.g., Rosenfeld (1992) *Cell* 68:143–155; Herz and Gerard (1993) *Proc. Natl. Acad. Sci. USA* 90:2812–2816), receptor-mediated DNA uptake (see e.g., Wu and Wu (1988) *J. Biol. Chem.* 263:14621; Wilson, et al. (1992) *J. Biol. Chem.* 267:963–967; U.S. Pat. No. 5,166,320), direct injection of DNA uptake (see e.g., Acsadi, et al. (1991) *Nature* 334:815–818; Wolff, et al. (1990) *Science* 247:1465–1468) or particle bombardment (see e.g., Cheng, et al. (1993) *Proc. Natl. Acad. Sci. USA* 90:4455–4459; Zelenin, et al. (1993) *FEBS Let.* 315:29–32).

Nucleic acid sequences encoding ATM kinase may be transferred into a fertilized oocyte of a non-human animal to create a transgenic animal which expresses ATM kinase in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. Exemplary examples of non-human animals include, but are not limited to, mice, goats, sheep, pigs, cows or other domestic farm animals. Such transgenic animals are useful, for example, for large-scale production of ATM kinase (gene pharming) or for basic research investigations.

A transgenic animal may be created, for example, by introducing a nucleic acid sequence encoding ATM kinase, typically linked to appropriate regulatory sequences, such as a constitutive or tissue-specific enhancer, into the male pronuclei of a fertilized oocyte, e.g., by microinjection, and allowing the oocyte to develop in a pseudopregnant female foster animal. Intron sequences and polyadenylation signals may also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009. A transgenic founder animal may be used to breed additional animals carrying the transgene. Transgenic animals carrying a transgene encoding ATM kinase may further be bred to other transgenic animals carrying other transgenes, e.g., p53.

Once produced, the ATM kinase may be recovered from the culture medium as a secreted polypeptide, although it also may be recovered from host cell lysates when directly expressed without a secretory signal. When ATM kinase is expressed in a recombinant cell other than one of human origin, the ATM kinase is completely free of proteins or polypeptides of human origin. However, it is necessary to purify ATM kinase from recombinant cell proteins or polypeptides to obtain preparations that are substantially homogeneous as to ATM kinase. As a first step, the culture medium or lysate is centrifuged to remove particulate cell debris. The membrane and soluble protein fractions are then separated. The ATM kinase may then be purified from the soluble protein fraction. ATM kinase thereafter is purified from contaminant soluble proteins and polypeptides, as exemplified herein or with, for example, the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; ligand affinity chromatography, and protein A Sepharose columns to remove contaminants such as IgG.

A further aspect of the invention provides a cell-based method of identifying agents which modulate activation of ATM kinase. As indicated, ATM kinase in an unperturbed cell is in an inactive state. Upon DNA damage, ATM kinase is autophosphorylated at $Ser^{1981}$ and converted to an active state. Therefore, an agent which modulates this autophosphorylation (i.e., activation) event may be identified in a screening assay by contacting a cell producing full-length ATM kinase or a fragment thereof retaining ATM kinase activity with an agent and determining the phosphorylation state of $Ser^{1981}$. Activation of ATM kinase may be modulated by blocking, inhibiting or decreasing activation (i.e., antagonizing) as well as activating, stimulating, or increasing activation (i.e., agonizing). A typical screening assay for antagonists comprises contacting an unperturbed cell with an agent, exposing said cell to a DNA damaging agent and determining whether said agent blocks or inhibits activation of ATM kinase. Enhancers of ATM kinase activation may also be identified in this assay as agents which increase the rate or amount of ATM kinase activation following DNA damage. A typical screening assay for agonists comprises contacting an unperturbed cell with an agent and determining whether said agent stimulates activation of ATM kinase. Methods for identifying the activation state of ATM kinase in a cell are provided herein. In a preferred embodiment, activation of ATM kinase is identified by determining the phosphorylation state of $Ser^{1981}$ using antibodies which specifically recognize the phosphorylation state of $Ser^{1981}$ of ATM kinase.

A further aspect of the invention provides a cell-free method of identifying agents which modulate ATM kinase activity. Soluble ATM kinase protein produced by the method disclosed herein is isolated as a monomer in an active state with an unphosphorylated $Ser^{1981}$ and upon addition of a phosphate donor, autophosphorylates $Ser^{1981}$ in the absence of DNA/DNA damage. Therefore, a typical screening assay using soluble ATM kinase protein comprises contacting soluble ATM kinase with an agent, exposing the soluble ATM kinase to a phosphate donor such as ATP, and detecting ATM kinase activity via autophosphorylation. The assay is carried out under suitable assay conditions for autophosphorylation, such as those exemplified herein. The phosphate donor may be added with or after the agent. It is preferred that autophosphorylation is detected using an antibody which specifically recognizes the phosphorylation state of $Ser^{1981}$ of ATM kinase. Agents which antagonize ATM kinase activity are useful as radiosensitizers or chemosensitizers in the treatment of a wide variety of human tumors.

Agents which may be screened using the screening assays provided herein encompass numerous chemical classes, though typically they are organic molecules, preferably small organic compounds having a molecular weight of more than 100 and less than about 2,500 daltons. Agents comprise functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups. Agents may also be found among biomolecules including peptides, antibodies, saccharides, fatty acids, steroids, purines, pyrimidines, derivatives, structural analogs or combinations thereof.

Agents are obtained from a wide variety of sources including libraries of synthetic or natural compounds.

Alternatively, the antibodies of this invention may be used for the design and synthesis of either peptide or non-peptide compounds (mimetics) specific to ATM kinase (see, e.g., Saragovi, et al (1991) *Science* 253:792–795).

A variety of other reagents may be included in the screening assays. These include reagents like salts, neutral proteins, e.g., albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, and the like may be used. The mixture of components may be added in any order that provides for the requisite binding.

Alternatively, the soluble ATM kinase provided herein may be used to generate a crystal structure of ATM kinase. Once the three-dimensional structure of ATM kinase is determined, a potential agent (antagonist or agonist) can be examined through the use of computer modeling using a docking program such as GRAM, DOCK, or AUTODOCK (Dunbrack, et al. (1997) *Folding & Design* 2:27–42). This procedure can include computer fitting of potential agents to ATM kinase to ascertain how well the shape and the chemical structure of the potential ligand will complement or interfere with, the binding of ATM kinase domain with a substrate. Computer programs can also be employed to estimate the attraction, repulsion, and steric hindrance of the agent. Generally the tighter the fit (e.g., the lower the steric hindrance, and/or the greater the attractive force) the more potent the potential agent will be since these properties are consistent with a tighter binding constraint. Furthermore, the more specificity in the design of a potential agent the more likely that the agent will not interfere with related mammalian proteins. This will minimize potential side-effects due to unwanted interactions with other proteins.

The invention is described in greater detail by the following non-limiting example.

EXAMPLE 1

Cell Culture, Immunofluorescence 293T cells, HeLa cells and 1070SK primary human foreskin fibroblasts (HFF) (>passage 20, ATCC) were cultured in Dulbecco's Modification of Eagle's Medium (DMEM) supplemented with 10% fetal bovine serum (FBS). GM00637 and GM09607 fibroblasts were grown in DMEM containing 15% FBS. GM00536 lymphoblast cells were grown in RPMI supplemented with 10% fetal calf serum. 293T cells were transfected using FUGENE™ (Roche, Indianapolis. Ind.) and HeLa cells, GM00637 and GM09607 with LIPOFECTAMINE™ (INVITROGEN™ Corp., Carlsbad, Calif.). Metabolic labeling was performed by pre-equilibrating cells in phosphate-free media for three hours prior to the addition of 0.5 mCi/ml $^{32}$P orthophosphate (PerkinElmer Life Sciences Inc., Boston, Mass.) for 30 minutes. Inhibition of DNA synthesis and analysis of G2/M checkpoint after irradiation was assessed using well-known methods (e.g., Xu, et al. (2001) *Mol. Cell. Biol.* 21:3445–3450). Wortmannin was added to samples on ice 15 minutes prior to reactions and 5 µM manganese and 1 µg sonicated calf thymus DNA were present or absent. Proteins were crosslinked by incubating cells in formaldehyde/phosphate-buffered saline (PBS) for 10 minutes at room temperature. Formaldehyde was washed out using PBS containing 100 mM glycine and immunoprecipitation was then performed. Hypotonic swelling was performed in PBS containing 0.45% glucose (w/v) and 1% FBS with the NaCl concentration reduced to either 50 mM or 100 mM. For immunofluoresence experiments, HFF grown on glass slides were fixed in 50% methanol/50% acetone for two hours at −20° C. Cells were incubated with primary antibodies at $\frac{1}{1000}$ (H2AXγ, Upstate, Charlottesville, Va.) and secondary antibodies at $\frac{1}{500}$ (Cy3 anti-mouse and FITC anti-rabbit; Jackson ImmunoResearch Laboratories, Inc., West Grove. Pa.) in PBS, 10% FBS for one hour.

EXAMPLE 2

Plasmids and Recombinant Protein Purification

FLAG®-tagged wild-type and kinase-inactive ATM are well-known in the art (e.g., Canman, et al. (1998) *Science* 281:1677–1679). Wild-type, FLAG®-tagged ATM was mutated using the QUIKCHANGE® site-directed mutagenesis kit (Stratagene, La Jolla, Calif.). The I-SceI expression plasmid is well-known in the art (Rouet, et al. (1994) *Proc. Natl. Acad. Sci. USA* 91:6064–6068). GST fusion proteins were expressed in BL21 from pGEX-4T-1 (Amersham Pharmacia Biotech, Uppsala, Sweden). Fusion proteins were purified and GST pull-down experiments performed by binding to glutathione-SEPHAROSE® beads (Sigma-Aldrich, St. Louis, Mo.) in PBS, 0.5% NP-40, 1 mM AEBSF and 1 mM DTT. Bound proteins were washed five times in the same buffer and eluted with 20 mM glutathione in 50 mM Tris/HCl, pH 8.0. ATM kinase domain was expressed from pET28 (NOVAGEN®, Inc., Madison, Wis.). Recombinant ATM with N-terminal 6×-His and FLAG® tags was expressed from pYES2 (INVITROGEN™, Carlsbad, Calif.) in JEL1, a protease-deficient *S. cerevisiae* strain that overexpresses the transcription factor GAL4 driven by the GAL1 promoter (Lindsley and Wang (1993) *J. Biol. Chem.* 268: 8096–8104). Following induction in 2% galactose for 16 hours yeast were lysed in 50 mM sodium phosphate pH 8.0, 300 mM NaCl, 0.4 µM aprotinin, 1 mM AEBSF, 1×soy trypsin inhibitor (Roche, Indianapolis. Ind.), 1.5 mM pepstatin and 42 µM leupeptin by three passages through a French press. Lysates were cleared by centrifugation at 35,000 rpm in a 45Ti centrifuge (Beckman COULTER®, Inc., Fullerton, Calif.). For anti-FLAG® M2 sepharose (Sigma-Aldrich, St. Louis, Mo.) affinity purification TWEEN® 20 and NP-40 were added to 1% and 0.5% respectively. FLAG® ATM was eluted in 100 µg/ml FLAG® peptide (Sigma-Aldrich, St. Louis, Mo.) in buffer A: 50 mM Tris (pH 7.5), 150 mM NaCl, 1% TWEEN® 20, 0.5% NP-40, 50 mM NaF, 1 mM AEBSF, and 1×protease inhibitor mixture (Roche, Indianapolis. Ind.). Size-exclusion chromatography was performed using a SUPERDEX® 200HR 10/30 column (Amersham Pharmacia Biotech, Uppsala, Sweden) in 50 mM sodium phosphate, pH 8.0 containing 150 mM NaCl. For Ni-NTA affinity purification, 20 mM imidazole was added to the lysates. 6×-His ATM was eluted from the nickel beads in 500 mM imidazole, pH 5.0, 300 mM NaCl and 2 mM EDTA.

EXAMPLE 3

Immunoprecipitation, in Vitro ATM Kinase Assays, and Peptide Mapping

Mammalian cell extracts were prepared in buffer A. Cleared supernatants were immunoprecipitated with anti-FLAG® M2 sepharose or anti-ATM D1611 (Alligood, et al. (2000) *Hybridoma* 19:317–321) and protein A/G agarose. Beads were washed twice with buffer A and twice with RIPA buffer. Co-immunoprecipitation was performed in buffer B: 50 mM Tris (pH 7.5), 150 mM NaCl, 0.5% TWEEN® 20, 0.2% NP-40, 50 mM NaF, 1 mM AEBSF, and 1×protease inhibitor mixture (Roche, Indianapolis. Ind.).

Ionizing irradiation induces phosphorylation of ATM at a single amino acid residue. The residue and consequence of ATM phosphorylation were examined by transiently transfecting 293T cells with either FLAG®-tagged wild-type or kinase-inactive ATM and metabolically labeling with $^{32}$P-orthophosphate. The amount of radioactive orthophosphate incorporated into transfected wild-type ATM thirty minutes after exposure of cells to 10 Gy IR was approximately five-fold greater than that seen in unirradiated cells. In contrast, no such increase was observed following irradiation of cells that had been transfected with kinase-inactive ATM. Similarly, the amount of phosphate incorporated into endogenous ATM in immortalized lymphoblasts was markedly increased following IR. Short labeling periods were required for these experiments since exposure of cells to these amounts of radioactive orthophosphate for longer than thirty minutes damages DNA and obscures differences between irradiated and unirradiated cells (Lim, et al. (2000) *Nature* 404:613–617; Siliciano, et al. (1997) *Genes Dev.* 11:3471–3481).

Incorporation of radioactive phosphate into ATM also occurs in in vitro assays of ATM kinase activity (Canman, et al. (1998) *Science* 281:1677–1679; Kim, et al. (1999) *J. Biol. Chem.* 274:37538–37543). For in vitro kinase assays, beads were washed twice with buffer A, twice with buffer A containing 0.5 M LiCl, and twice with kinase buffer: 20 mM HEPES (pH 7.5), 50 mM NaCl, 10 mM MgCl$_2$ and 10 mM MnCl$_2$. ATM kinase reactions were performed at 30° C. for five minutes in 50 µl of kinase buffer containing 10 µCi of [γ-$^{32}$P] ATP and 1 µg of GST-fusion substrate. In vitro phosphorylation of ATM was not seen with the kinase-inactive ATM protein; was inhibited by exposure to 30 nM of the PI-3K inhibitor wortmannin; was dependent on the addition of the divalent cation manganese; and was not dependent on addition of exogenous DNA. Identical properties are characteristic of ATM in its phosphorylation of target substrates: a concentration of 30 nM wortmannin effectively inhibits ATM kinase activity (Sarkaria, et al. (1998) *Cancer Res.* 58:4375–4382); its activity requires the presence of manganese (Canman, et al. (1998) *Science* 281:1677–1679; Kim, et al. (1999) *J. Biol. Chem.* 274: 37538–37543); and exogenous DNA does not enhance its activity after immunoprecipitation from cells (Kim, et al. (1999) *J. Biol. Chem.* 274:37538–37543). Together with the observation that ATM kinase activity was required for the increase in ATM phosphorylation seen during metabolic labeling of cells, these findings indicate that ATM phosphorylates itself.

The site of phosphorylation in ATM was identified by radioactively labeling ATM protein, digesting with trypsin, and analyzing tryptic phosphopeptides by sequential two-dimensional (2-D) electrophoresis and chromatography. Tryptic digestion of FLAG® ATM immobilized on nitrocellulose, 2-D resolution (electrophoresis and chromatography), manual Edman degradation and V8 digestion of peptides isolated from thin-layer chromatography plates were performed using well-known methods (Meisenhelder et al. Current Protocols in Molecular Biology. Ausubel, F. M. et al. (eds.) (1999)). A single de novo phosphorylated peptide was identified in both transfected FLAG®-tagged ATM and in endogenous ATM isolated from irradiated cells. Since the increase in phosphorylation of this peptide was seen in vivo with wild-type, but not kinase-inactive ATM, this event is consistent with IR-inducible ATM autophosphorylation.

The ATM amino acid residue phosphorylated following IR was determined. The phosphopeptide identified by thin layer chromatography was isolated and subjected to acid hydrolysis. Resolution of the labeled phosphoamino acid by 2-D electrophoresis with unlabeled phosphoamino acid markers revealed phosphoserine. There are 121 predicted tryptic peptides in ATM containing a single phosphoserine residue and many additional peptides containing two or more. Direct identification of the phosphopeptide by automated sequencing and mass spectrometry failed, at least in part due to difficulties in obtaining sufficient quantities of material.

The predicted migrations of tryptic serine-containing phosphopeptides in ATM eliminated many candidates. Forty-one tryptic serine phosphopeptides, whose theoretical migration satisfied criteria for that of the principal peptide at pH 1.9 and pH 4.72, were synthesized and subjected to 2-D electrophoresis and chromatography along with tryptic digests of radioactively labeled ATM. The theoretical and observed migrations of the 41 peptides were coincident at both pH's but this nonetheless failed to identify the radiolabeled phosphopeptide.

Many kinases are activated by phosphorylation within their kinase domains (Johnson and Noble (1996) *Cell* 85:149–158), therefore, each serine in the kinase domain, as well as several other Ser-Gln sequences in ATM, were subjected to site-directed mutagenesis. Individual serines in wild-type, FLAG®-tagged ATM were mutated to glycine or alanine and the mutants were expressed, immunoprecipitated and allowed to autophosphorylate in vitro. The labeled, mutant ATM proteins were then digested with trypsin and the resulting tryptic phosphopeptides were resolved by 2-D mapping. Surprisingly, the major phosphopeptide was still detected on 2-D maps of each ATM mutant, all of which retained kinase activity. Therefore, none of the serines in the kinase domain of ATM are required for its kinase activity.

The major ATM phosphopeptide was identified by use of secondary proteolytic and chemical cleavage of the primary phosphopeptide. After in vivo radioactive labeling of ATM protein and purification of the phosphopeptide from the thin layer chromatography plate, the purified tryptic phosphopeptide was digested with V8 protease. The appearance of a peptide with a new mobility on 2-D maps dictated the presence of a glutamic acid in the peptide. Furthermore, an unchanged chromatographic mobility after cyanogen bromide treatment of the purified tryptic phosphopeptide in formic acid indicated that it did not contain methionine.

Manual Edman degradation was then performed on both the tryptic serine phosphopeptide and the derived V8/tryptic phosphopeptide. Resolution of the Edman degradation products revealed a secondary spot in each cycle suggesting a derivatized peptide. If the peptide being treated in the Edman reaction contains a C-terminal lysine, the phenylisothiocyanate treatment followed by acid treatment causes a derivatization of the lysine ε-amino group (Meisenhelder et al. Current Protocols in Molecular Biology. Ausubel, F. M. et al. (eds.) (1999)). Thus, the manual Edman reactions indicated that the phosphopeptide of interest had a C-terminal lysine. The second cycle of Edman degradation resulted in the generation of free phosphate from the V8/tryptic phosphopeptide. Thus, the phosphorylated serine is two amino acid residues to the C-terminal side of a glutamic acid residue. Further cycles of Edman degradation were required to release the phosphate from the original tryptic phosphopeptide, with generation of some free phosphate at cycle eight and substantial release at cycle nine. Thus, the phosphorylated serine in the larger peptide was eight or nine amino acid residues to the C-terminal side of either a lysine or arginine residue.

Although inefficiencies in the manual Edman degradation process cause difficulties when more than five or six cycles are required for amino acid release (Meisenhelder et al. Current Protocols in Molecular Biology. Ausubel, F. M. et al. (eds.) (1999)), a partial sequence was obtained for the major serine phosphopeptide of Xaa$_{5-6}$-Glu-Xaa-Ser-Xaa$_n$-Lys (SEQ ID NO: 3) (where Xaa is any amino acid other than Met, the N-terminus contains 5–6 residues, and the sequence preceding the C-terminal Lys is of unknown length, n). The only tryptic peptide in ATM which meets these sequence requirements is the 19 residue peptide 1974-Ser-Leu-Ala-Phe-Glu-Glu-Gly-Ser-Gln-Ser-Thr-Thr-Ile-Ser-Ser-Leu-Ser-Glu-Lys-1992 (SEQ ID NO: 4). In addition, since V8 protease does not cleave at every glutamic acid in a peptide sequence, the adjacent residues Glu$^{1978}$ and Glu$^{1979}$ explain the release of free phosphate at both cycles two and three in the manual Edman degradation of the V8/tryptic phosphopeptide. The V8 phosphopeptide was likely a mixture of two peptides that were unresolved on the 2-D map at pH 1.9, one of which had been cleaved at Glu$^{1978}$ and one at Glu$^{1979}$. It is noted that V8 did not digest the tryptic phosphopeptide at Glu$^{1991}$ since the derivatization of Lys$^{1992}$ in the manual Edman degradation of the V8/tryptic phosphopeptide was seen. Ser$^{1981}$ in ATM is conserved in mouse and Xenopus ATM, but is not found in suspected homologues of less complex metazoans and is located in the N-terminus of the FAT domain, a region of approximately 500 amino acid residues with some conservation across the PI-3K family of kinases including Frap, ATM and Trapp (Bosotti, el al. (2000) *Trends Biochem. Sci.* 25:225–227). It is also noted that this is an 'Ser-Gln' site, thus indicating either an autophosphorylation event or phosphorylation by an ATM family member.

EXAMPLE 4

Western Blotting and Antisera Production

Western blotting was performed with anti-FLAG®. M5 (Sigma-Aldrich, St. Louis, Mo.), anti-ATM MAT3, anti-GST (Amersham Pharmacia Biotech, Uppsala, Sweden) or anti-6x-His (Sigma-Aldrich, St. Louis, Mo.). Anti-Ser$^{1981}$ and anti-Ser$^{1981}$-P specific antibodies were generated by immunizing rabbits with KLH-conjugated synthetic peptides Ser-Leu-Ala-Phe-Glu-Glu-Gly-Ser-Gln-Ser-Thr-Thr-Ile-Ser-Ser (SEQ ID NO: 5) (three animals) and Ser-Leu-Ala-Phe-Glu-Glu-Gly-Ser(P)-Gln-Ser-Thr-Thr-Ile-Ser-Ser (SEQ ID NO: 6) (6 animals), respectively (Rockland Immunochemicals, Gilbertsville, Pa.).

EXAMPLE 5

Autophosphorylation

Autophosphorylation of Ser$^{1981}$ was determined using glutathione-S-transferase (GST) fusion proteins containing various lengths of ATM as substrates of the ATM kinase in in vitro kinase reactions. A polypeptide containing the appropriate serine residue at 1981 was an excellent in vitro substrate, whereas a Ser$^{1981}$→Ala mutant was not phosphorylated by ATM whether the read-out was incorporation of radioactive phosphate or binding by the α-Ser$^{1981}$-P antibody. In addition, wortmannin concentrations of 20 μM or more effectively inhibited phosphorylation of Ser$^{1981}$ following irradiation of human diploid fibroblasts. This concentration of wortmannin inhibits both ATM and DNA-dependent protein kinase (DNA-PK), but not ataxia- and Rad3-related protein (ATR), in vivo (Sarkaria, et al. (1998) *Cancer Res.* 58:4375–4382). To exclude DNA-PK as a responsible kinase, phosphorylation of Ser$^{1981}$ was determined in a cell line lacking DNA-PK activity. The kinetics and levels of IR-induced phosphorylation of Ser$^{1981}$ were identical to those in a similar cell line containing DNA-PK activity.

In vivo experiments demonstrated that optimal phosphorylation of ATM was dependent on the presence of active ATM kinase, however, the cells used contained endogenous wild-type ATM. Thus, even the kinase-inactive mutant of ATM was phosphorylated to some extent in these cells. The importance of ATM kinase activity in the phosphorylation of Ser$^{1981}$ was further analyzed using constructs encoding wild-type, kinase-inactive, and Ser$^{1981}$→Ala ATM transfected into A-T cells such that the only potential source of ATM kinase activity was the transgene being utilized. All of these constructs were expressed at similar levels in A-T cells, but only wild-type ATM was recognized by α-Ser$^{1981}$-P, and its binding was increased several-fold within 30 minutes after exposure to 10 Gy IR. Although some phosphorylation of kinase-inactive ATM was observed following transfection into 293T cells, which contain endogenous ATM activity, transfection into a cell line that lacked ATM kinase activity showed no detectable phosphorylation on Ser$^{1981}$. Therefore, phosphorylation of Ser$^{1981}$ depends on the activity of the ATM kinase itself and the phosphorylation of transfected kinase-inactive ATM must occur in trans.

Mutating Ser$^{1981}$ did not abrogate ATM kinase activity in vitro, but conferred dominant inhibitory activity in cells. Expression vectors encoding wild-type and Ser$^{1981}$→Ala ATM proteins were transfected into A-T fibroblasts and kinase activity was assessed by in vitro kinase assays performed with the immunoprecipitated ATM proteins. Both wild-type and Ser$^{1981}$→Ala mutant ATM exhibited in vitro kinase activity directed against a peptide containing the Ser$_{15}$ target sequence in p53. To explore the in vivo activity of the Ser 1981→Ala mutant, nucleic acid sequences encoding ATM kinase were introduced into HeLa cells and the integrity of their ATM-dependent, IR-induced G2 and S-phase checkpoints was examined. Despite its kinase activity in the in vitro assay, Ser$^{1981}$→Ala ATM mimicked kinase-inactive ATM in inhibiting both the IR-induced G2 checkpoint and S-phase replication arrest. Consistent with its abrogation of the IR-induced cell cycle checkpoints, the transfected Ser$^{1981}$→Ala mutant also blocked the IR-induced phosphorylation of endogenous ATM protein on Ser$^{1981}$. Thus, whereas phosphorylation of ATM on Ser$^{1981}$ does not appear to be required for kinase activity in vitro, expression of Ser$^{1981}$→Ala ATM effectively inhibits the cellular activities of endogenous ATM in a dominant-inhibitory manner.

What is claimed is:

1. An antibody specific for Ataxia-Telangiectasia Mutated kinase wherein the antibody specifically recognizes the phosphorylation state of a serine corresponding to residue 1981 of Ataxia-Telangiectasia Mutated kinase of SEQ ID NO: 1 in a peptide sequence comprising Ser-Leu-Ala-Phe-Glu-Glu-Gly-Ser-Gln-Ser-Thr-Thr-Ile-Ser-Ser (SEQ ID NO: 5) or Ser-Leu-Ala-Phe-Glu-Glu-Gly-Ser(P)-Gln-Ser-Thr-Thr-Ile-Ser-Ser (SEQ ID NO: 6), in which Ser(P) indicates phosphorylation of serine.

2. The antibody of claim 1, wherein the antibody specifically recognizes a phosphorylated serine corresponding to residue 1981 of Ataxia-Telangiectasia Mutated kinase of SEQ ID NO: 1.

3. The antibody of claim 2, wherein the antibody is a polyclonal antibody or a fragment thereof.

4. The antibody of claim 2, wherein the antibody is a monoclonal antibody or a fragment thereof.

5. The antibody of claim 1, wherein the antibody specifically recognizes an unphosphorylated serine corresponding to residue 1981 of Ataxia-Telangiectasia Mutated kinase of SEQ ID NO: 1.

6. The antibody of claim 5, wherein the antibody is a polyclonal antibody or a fragment thereof.

7. The antibody of claim 5, wherein the antibody is a monoclonal antibody or a fragment thereof.

8. A kit for the detecting a DNA damaging agent in a sample comprising an antibody of claim 1.

9. The kit of claim 8 further comprising Ataxia-Telangiectasia Mutated kinase protein.

* * * * *

SEQUENCE LISTING

<160> NUMBER OF SEQ ID NOS: 6

<210> SEQ ID NO 1
<211> LENGTH: 3056
<212> TYPE: PRT
<213> ORGANISM: Homo sapiens

<400> SEQUENCE: 1

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

-continued

```
Leu Ile Arg Asp Pro Glu Thr Ile Lys His Leu Asp Arg His Ser Asp
            35                  40                  45

Ser Lys Gln Gly Lys Tyr Leu Asn Trp Asp Ala Val Phe Arg Phe Leu
 50                  55                  60

Gln Lys Tyr Ile Gln Lys Glu Thr Glu Cys Leu Arg Ile Ala Lys Pro
 65                  70                  75                  80

Asn Val Ser Ala Ser Thr Gln Ala Ser Arg Gln Lys Lys Met Gln Glu
                 85                  90                  95

Ile Ser Ser Leu Val Lys Tyr Phe Ile Lys Cys Ala Asn Arg Arg Ala
                100                 105                 110

Pro Arg Leu Lys Cys Gln Glu Leu Leu Asn Tyr Ile Met Asp Thr Val
            115                 120                 125

Lys Asp Ser Ser Asn Gly Ala Ile Tyr Gly Ala Asp Cys Ser Asn Ile
        130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
    370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
        435                 440                 445
```

-continued

```
Gly Glu Arg Thr Pro Tyr Val Leu Arg Cys Leu Thr Glu Val Ala Leu
    450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
    530                 535                 540

Ala Leu Thr Thr Ser Ile Val Pro Gly Ala Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
                580                 585                 590

Thr Glu Val Pro Pro Ile Leu His Ser Asn Phe Pro His Leu Val Leu
            595                 600                 605

Glu Lys Ile Leu Val Ser Leu Thr Met Lys Asn Cys Lys Ala Ala Met
        610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Leu Phe Leu Gln Thr Thr
                645                 650                 655

Phe Asp Lys Met Asp Phe Leu Thr Ile Val Arg Glu Cys Gly Ile Glu
                660                 665                 670

Lys His Gln Ser Ser Ile Gly Phe Ser Val His Gln Asn Leu Lys Glu
            675                 680                 685

Ser Leu Asp Arg Cys Leu Leu Gly Leu Ser Glu Gln Leu Leu Asn Asn
        690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
    770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Thr Asn Gly Asn Leu Met Glu
        835                 840                 845

Val Glu Asp Gln Ser Ser Met Asn Leu Phe Asn Asp Tyr Pro Asp Ser
    850                 855                 860

Ser Val Ser Asp Ala Asn Glu Pro Gly Glu Ser Gln Ser Thr Ile Gly
```

```
                865                 870                 875                 880
Ala Ile Asn Pro Leu Ala Glu Glu Tyr Leu Ser Lys Gln Asp Leu Leu
                    885                 890                 895

Phe Leu Asp Met Leu Lys Phe Leu Cys Leu Cys Val Thr Thr Ala Gln
                900                 905                 910

Thr Asn Thr Val Ser Phe Arg Ala Ala Asp Ile Arg Arg Lys Leu Leu
                915                 920                 925

Met Leu Ile Asp Ser Ser Thr Leu Glu Pro Thr Lys Ser Leu His Leu
        930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
                980                 985                 990

His Val Leu His Val Val Lys Asn  Leu Gly Gln Ser Asn  Met Asp Ser
                995                 1000                1005

Glu Asn  Thr Arg Asp Ala Gln  Gly Gln Phe Leu Thr  Val Ile Gly
1010                1015                1020

Ala Phe  Trp His Leu Thr Lys  Glu Arg Lys Tyr Ile  Phe Ser Val
1025                1030                1035

Arg Met  Ala Leu Val Asn Cys  Leu Lys Thr Leu Leu  Glu Ala Asp
1040                1045                1050

Pro Tyr  Ser Lys Trp Ala Ile  Leu Asn Val Met Gly  Lys Asp Phe
1055                1060                1065

Pro Val  Asn Glu Val Phe Thr  Gln Phe Leu Ala Asp  Asn His His
1070                1075                1080

Gln Val  Arg Met Leu Ala Ala  Glu Ser Ile Asn Arg  Leu Phe Gln
1085                1090                1095

Asp Thr  Lys Gly Asp Ser Ser  Arg Leu Leu Lys Ala  Leu Pro Leu
1100                1105                1110

Lys Leu  Gln Gln Thr Ala Phe  Glu Asn Ala Tyr Leu  Lys Ala Gln
1115                1120                1125

Glu Gly  Met Arg Glu Met Ser  His Ser Ala Glu Asn  Pro Glu Thr
1130                1135                1140

Leu Asp  Glu Ile Tyr Asn Arg  Lys Ser Val Leu Leu  Thr Leu Ile
1145                1150                1155

Ala Val  Val Leu Ser Cys Ser  Pro Ile Cys Glu Lys  Gln Ala Leu
1160                1165                1170

Phe Ala  Leu Cys Lys Ser Val  Lys Glu Asn Gly Leu  Glu Pro His
1175                1180                1185

Leu Val  Lys Lys Val Leu Glu  Lys Val Ser Glu Thr  Phe Gly Tyr
1190                1195                1200

Arg Arg  Leu Glu Asp Phe Met  Ala Ser His Leu Asp  Tyr Leu Val
1205                1210                1215

Leu Glu  Trp Leu Asn Leu Gln  Asp Thr Glu Tyr Asn  Leu Ser Ser
1220                1225                1230

Phe Pro  Phe Ile Leu Leu Asn  Tyr Thr Asn Ile Glu  Asp Phe Tyr
1235                1240                1245

Arg Ser  Cys Tyr Lys Val Leu  Ile Pro His Leu Val  Ile Arg Ser
1250                1255                1260

His Phe  Asp Glu Val Lys Ser  Ile Ala Asn Gln Ile  Gln Glu Asp
1265                1270                1275
```

-continued

```
Trp Lys Ser Leu Leu Thr Asp Cys Phe Pro Lys Ile Leu Val Asn
    1280                1285                1290

Ile Leu Pro Tyr Phe Ala Tyr Glu Gly Thr Arg Asp Ser Gly Met
    1295                1300                1305

Ala Gln Gln Arg Glu Thr Ala Thr Lys Val Tyr Asp Met Leu Lys
    1310                1315                1320

Ser Glu Asn Leu Leu Gly Lys Gln Ile Asp His Leu Phe Ile Ser
    1325                1330                1335

Asn Leu Pro Glu Ile Val Val Glu Leu Leu Met Thr Leu His Glu
    1340                1345                1350

Pro Ala Asn Ser Ser Ala Ser Gln Ser Thr Asp Leu Cys Asp Phe
    1355                1360                1365

Ser Gly Asp Leu Asp Pro Ala Pro Asn Pro Pro His Phe Pro Ser
    1370                1375                1380

His Val Ile Lys Ala Thr Phe Ala Tyr Ile Ser Asn Cys His Lys
    1385                1390                1395

Thr Lys Leu Lys Ser Ile Leu Glu Ile Leu Ser Lys Ser Pro Asp
    1400                1405                1410

Ser Tyr Gln Lys Ile Leu Leu Ala Ile Cys Glu Gln Ala Ala Glu
    1415                1420                1425

Thr Asn Asn Val Tyr Lys Lys His Arg Ile Leu Lys Ile Tyr His
    1430                1435                1440

Leu Phe Val Ser Leu Leu Leu Lys Asp Ile Lys Ser Gly Leu Gly
    1445                1450                1455

Gly Ala Trp Ala Phe Val Leu Arg Asp Val Ile Tyr Thr Leu Ile
    1460                1465                1470

His Tyr Ile Asn Gln Arg Pro Ser Cys Ile Met Asp Val Ser Leu
    1475                1480                1485

Arg Ser Phe Ser Leu Cys Cys Asp Leu Leu Ser Gln Val Cys Gln
    1490                1495                1500

Thr Ala Val Thr Tyr Cys Lys Asp Ala Leu Glu Asn His Leu His
    1505                1510                1515

Val Ile Val Gly Thr Leu Ile Pro Leu Val Tyr Glu Gln Val Glu
    1520                1525                1530

Val Gln Lys Gln Val Leu Asp Leu Leu Lys Tyr Leu Val Ile Asp
    1535                1540                1545

Asn Lys Asp Asn Glu Asn Leu Tyr Ile Thr Ile Lys Leu Leu Asp
    1550                1555                1560

Pro Phe Pro Asp His Val Val Phe Lys Asp Leu Arg Ile Thr Gln
    1565                1570                1575

Gln Lys Ile Lys Tyr Ser Arg Gly Pro Phe Ser Leu Leu Glu Glu
    1580                1585                1590

Ile Asn His Phe Leu Ser Val Ser Val Tyr Asp Ala Leu Pro Leu
    1595                1600                1605

Thr Arg Leu Glu Gly Leu Lys Asp Leu Arg Arg Gln Leu Glu Leu
    1610                1615                1620

His Lys Asp Gln Met Val Asp Ile Met Arg Ala Ser Gln Asp Asn
    1625                1630                1635

Pro Gln Asp Gly Ile Met Val Lys Leu Val Val Asn Leu Leu Gln
    1640                1645                1650

Leu Ser Lys Met Ala Ile Asn His Thr Gly Glu Lys Glu Val Leu
    1655                1660                1665
```

```
Glu Ala Val Gly Ser Cys Leu Gly Glu Val Gly Pro Ile Asp Phe
1670            1675                1680

Ser Thr Ile Ala Ile Gln His Ser Lys Asp Ala Ser Tyr Thr Lys
1685            1690                1695

Ala Leu Lys Leu Phe Glu Asp Lys Glu Leu Gln Trp Thr Phe Ile
1700            1705                1710

Met Leu Thr Tyr Leu Asn Asn Thr Leu Val Glu Asp Cys Val Lys
1715            1720                1725

Val Arg Ser Ala Ala Val Thr Cys Leu Lys Asn Ile Leu Ala Thr
1730            1735                1740

Lys Thr Gly His Ser Phe Trp Glu Ile Tyr Lys Met Thr Thr Asp
1745            1750                1755

Pro Met Leu Ala Tyr Leu Gln Pro Phe Arg Thr Ser Arg Lys Lys
1760            1765                1770

Phe Leu Glu Val Pro Arg Phe Asp Lys Glu Asn Pro Phe Glu Gly
1775            1780                1785

Leu Asp Asp Ile Asn Leu Trp Ile Pro Leu Ser Glu Asn His Asp
1790            1795                1800

Ile Trp Ile Lys Thr Leu Thr Cys Ala Phe Leu Asp Ser Gly Gly
1805            1810                1815

Thr Lys Cys Glu Ile Leu Gln Leu Leu Lys Pro Met Cys Glu Val
1820            1825                1830

Lys Thr Asp Phe Cys Gln Thr Val Leu Pro Tyr Leu Ile His Asp
1835            1840                1845

Ile Leu Leu Gln Asp Thr Asn Glu Ser Trp Arg Asn Leu Leu Ser
1850            1855                1860

Thr His Val Gln Gly Phe Phe Thr Ser Cys Leu Arg His Phe Ser
1865            1870                1875

Gln Thr Ser Arg Ser Thr Thr Pro Ala Asn Leu Asp Ser Glu Ser
1880            1885                1890

Glu His Phe Phe Arg Cys Cys Leu Asp Lys Lys Ser Gln Arg Thr
1895            1900                1905

Met Leu Ala Val Val Asp Tyr Met Arg Arg Gln Lys Arg Pro Ser
1910            1915                1920

Ser Gly Thr Ile Phe Asn Asp Ala Phe Trp Leu Asp Leu Asn Tyr
1925            1930                1935

Leu Glu Val Ala Lys Val Ala Gln Ser Cys Ala Ala His Phe Thr
1940            1945                1950

Ala Leu Leu Tyr Ala Glu Ile Tyr Ala Asp Lys Lys Ser Met Asp
1955            1960                1965

Asp Gln Glu Lys Arg Ser Leu Ala Phe Glu Glu Gly Ser Gln Ser
1970            1975                1980

Thr Thr Ile Ser Ser Leu Ser Glu Lys Ser Lys Glu Glu Thr Gly
1985            1990                1995

Ile Ser Leu Gln Asp Leu Leu Leu Glu Ile Tyr Arg Ser Ile Gly
2000            2005                2010

Glu Pro Asp Ser Leu Tyr Gly Cys Gly Gly Gly Lys Met Leu Gln
2015            2020                2025

Pro Ile Thr Arg Leu Arg Thr Tyr Glu His Glu Ala Met Trp Gly
2030            2035                2040

Lys Ala Leu Val Thr Tyr Asp Leu Glu Thr Ala Ile Pro Ser Ser
2045            2050                2055
```

-continued

```
Thr Arg Gln Ala Gly Ile Ile Gln Ala Leu Gln Asn Leu Gly Leu
    2060            2065            2070

Cys His Ile Leu Ser Val Tyr Leu Lys Gly Leu Asp Tyr Glu Asn
    2075            2080            2085

Lys Asp Trp Cys Pro Glu Leu Glu Leu His Tyr Gln Ala Ala
    2090            2095            2100

Trp Arg Asn Met Gln Trp Asp His Cys Thr Ser Val Ser Lys Glu
    2105            2110            2115

Val Glu Gly Thr Ser Tyr His Glu Ser Leu Tyr Asn Ala Leu Gln
    2120            2125            2130

Ser Leu Arg Asp Arg Glu Phe Ser Thr Phe Tyr Glu Ser Leu Lys
    2135            2140            2145

Tyr Ala Arg Val Lys Glu Val Glu Glu Met Cys Lys Arg Ser Leu
    2150            2155            2160

Glu Ser Val Tyr Ser Leu Tyr Pro Thr Leu Ser Arg Leu Gln Ala
    2165            2170            2175

Ile Gly Glu Leu Glu Ser Ile Gly Glu Leu Phe Ser Arg Ser Val
    2180            2185            2190

Thr His Arg Gln Leu Ser Glu Val Tyr Ile Lys Trp Gln Lys His
    2195            2200            2205

Ser Gln Leu Leu Lys Asp Ser Asp Phe Ser Phe Gln Glu Pro Ile
    2210            2215            2220

Met Ala Leu Arg Thr Val Ile Leu Glu Ile Leu Met Glu Lys Glu
    2225            2230            2235

Met Asp Asn Ser Gln Arg Glu Cys Ile Lys Asp Ile Leu Thr Lys
    2240            2245            2250

His Leu Val Glu Leu Ser Ile Leu Ala Arg Thr Phe Lys Asn Thr
    2255            2260            2265

Gln Leu Pro Glu Arg Ala Ile Phe Gln Ile Lys Gln Tyr Asn Ser
    2270            2275            2280

Val Ser Cys Gly Val Ser Glu Trp Gln Leu Glu Glu Ala Gln Val
    2285            2290            2295

Phe Trp Ala Lys Lys Glu Gln Ser Leu Ala Leu Ser Ile Leu Lys
    2300            2305            2310

Gln Met Ile Lys Lys Leu Asp Ala Ser Cys Ala Ala Asn Asn Pro
    2315            2320            2325

Ser Leu Lys Leu Thr Tyr Thr Glu Cys Leu Arg Val Cys Gly Asn
    2330            2335            2340

Trp Leu Ala Glu Thr Cys Leu Glu Asn Pro Ala Val Ile Met Gln
    2345            2350            2355

Thr Tyr Leu Glu Lys Ala Val Glu Val Ala Gly Asn Tyr Asp Gly
    2360            2365            2370

Glu Ser Ser Asp Glu Leu Arg Asn Gly Lys Met Lys Ala Phe Leu
    2375            2380            2385

Ser Leu Ala Arg Phe Ser Asp Thr Gln Tyr Gln Arg Ile Glu Asn
    2390            2395            2400

Tyr Met Lys Ser Ser Glu Phe Glu Asn Lys Gln Ala Leu Leu Lys
    2405            2410            2415

Arg Ala Lys Glu Glu Val Gly Leu Leu Arg Glu His Lys Ile Gln
    2420            2425            2430

Thr Asn Arg Tyr Thr Val Lys Val Gln Arg Glu Leu Glu Leu Asp
    2435            2440            2445
```

-continued

```
Glu Leu Ala Leu Arg Ala Leu Lys Glu Asp Arg Lys Arg Phe Leu
2450                2455                2460

Cys Lys Ala Val Glu Asn Tyr Ile Asn Cys Leu Leu Ser Gly Glu
2465                2470                2475

Glu His Asp Met Trp Val Phe Arg Leu Cys Ser Leu Trp Leu Glu
2480                2485                2490

Asn Ser Gly Val Ser Glu Val Asn Gly Met Met Lys Arg Asp Gly
2495                2500                2505

Met Lys Ile Pro Thr Tyr Lys Phe Leu Pro Leu Met Tyr Gln Leu
2510                2515                2520

Ala Ala Arg Met Gly Thr Lys Met Met Gly Gly Leu Gly Phe His
2525                2530                2535

Glu Val Leu Asn Asn Leu Ile Ser Arg Ile Ser Met Asp His Pro
2540                2545                2550

His His Thr Leu Phe Ile Ile Leu Ala Leu Ala Asn Ala Asn Arg
2555                2560                2565

Asp Glu Phe Leu Thr Lys Pro Glu Val Ala Arg Arg Ser Arg Ile
2570                2575                2580

Thr Lys Asn Val Pro Lys Gln Ser Ser Gln Leu Asp Glu Asp Arg
2585                2590                2595

Thr Glu Ala Ala Asn Arg Ile Ile Cys Thr Ile Arg Ser Arg Arg
2600                2605                2610

Pro Gln Met Val Arg Ser Val Glu Ala Leu Cys Asp Ala Tyr Ile
2615                2620                2625

Ile Leu Ala Asn Leu Asp Ala Thr Gln Trp Lys Thr Gln Arg Lys
2630                2635                2640

Gly Ile Asn Ile Pro Ala Asp Gln Pro Ile Thr Lys Leu Lys Asn
2645                2650                2655

Leu Glu Asp Val Val Val Pro Thr Met Glu Ile Lys Val Asp His
2660                2665                2670

Thr Gly Glu Tyr Gly Asn Leu Val Thr Ile Gln Ser Phe Lys Ala
2675                2680                2685

Glu Phe Arg Leu Ala Gly Gly Val Asn Leu Pro Lys Ile Ile Asp
2690                2695                2700

Cys Val Gly Ser Asp Gly Lys Glu Arg Arg Gln Leu Val Lys Gly
2705                2710                2715

Arg Asp Asp Leu Arg Gln Asp Ala Val Met Gln Gln Val Phe Gln
2720                2725                2730

Met Cys Asn Thr Leu Leu Gln Arg Asn Thr Glu Thr Arg Lys Arg
2735                2740                2745

Lys Leu Thr Ile Cys Thr Tyr Lys Val Val Pro Leu Ser Gln Arg
2750                2755                2760

Ser Gly Val Leu Glu Trp Cys Thr Gly Thr Val Pro Ile Gly Glu
2765                2770                2775

Phe Leu Val Asn Asn Glu Asp Gly Ala His Lys Arg Tyr Arg Pro
2780                2785                2790

Asn Asp Phe Ser Ala Phe Gln Cys Gln Lys Lys Met Met Glu Val
2795                2800                2805

Gln Lys Lys Ser Phe Glu Glu Lys Tyr Glu Val Phe Met Asp Val
2810                2815                2820

Cys Gln Asn Phe Gln Pro Val Phe Arg Tyr Phe Cys Met Glu Lys
2825                2830                2835
```

```
Phe Leu Asp Pro Ala Ile Trp Phe Glu Lys Arg Leu Ala Tyr Thr
    2840                2845                2850
Arg Ser Val Ala Thr Ser Ser Ile Val Gly Tyr Ile Leu Gly Leu
    2855                2860                2865
Gly Asp Arg His Val Gln Asn Ile Leu Ile Asn Glu Gln Ser Ala
    2870                2875                2880
Glu Leu Val His Ile Asp Leu Gly Val Ala Phe Glu Gln Gly Lys
    2885                2890                2895
Ile Leu Pro Thr Pro Glu Thr Val Pro Phe Arg Leu Thr Arg Asp
    2900                2905                2910
Ile Val Asp Gly Met Gly Ile Thr Gly Val Glu Gly Val Phe Arg
    2915                2920                2925
Arg Cys Cys Glu Lys Thr Met Glu Val Met Arg Asn Ser Gln Glu
    2930                2935                2940
Thr Leu Leu Thr Ile Val Glu Val Leu Leu Tyr Asp Pro Leu Phe
    2945                2950                2955
Asp Trp Thr Met Asn Pro Leu Lys Ala Leu Tyr Leu Gln Gln Arg
    2960                2965                2970
Pro Glu Asp Glu Thr Glu Leu His Pro Thr Leu Asn Ala Asp Asp
    2975                2980                2985
Gln Glu Cys Lys Arg Asn Leu Ser Asp Ile Asp Gln Ser Phe Asp
    2990                2995                3000
Lys Val Ala Glu Arg Val Leu Met Arg Leu Gln Glu Lys Leu Lys
    3005                3010                3015
Gly Val Glu Glu Gly Thr Val Leu Ser Val Gly Gly Gln Val Asn
    3020                3025                3030
Leu Leu Ile Gln Gln Ala Ile Asp Pro Lys Asn Leu Ser Arg Leu
    3035                3040                3045
Phe Pro Gly Trp Lys Ala Trp Val
    3050                3055

<210> SEQ ID NO 2
<211> LENGTH: 7
<212> TYPE: PRT
<213> ORGANISM: Artificial Sequence
<220> FEATURE:
<223> OTHER INFORMATION: Substrate recognition sequence.
<220> FEATURE:
<221> NAME/KEY: MISC_FEATURE
<222> LOCATION: (1)..(1)
<223> OTHER INFORMATION: "Xaa" is defined as a hydrophobic amino acid.
<220> FEATURE:
<221> NAME/KEY: MISC_FEATURE
<222> LOCATION: (2)..(2)
<223> OTHER INFORMATION: "Xaa" is defined as any amino acid.
<220> FEATURE:
<221> NAME/KEY: MISC_FEATURE
<222> LOCATION: (3)..(3)
<223> OTHER INFORMATION: "Xaa" is defined as a hydrophobic amino acid or
      aspartic acid.
<220> FEATURE:
<221> NAME/KEY: MISC_FEATURE
<222> LOCATION: (6)..(7)
<223> OTHER INFORMATION: "Xaa" is defined as any amino acid.

<400> SEQUENCE: 2

Xaa Xaa Xaa Ser Gln Xaa Xaa
1               5

<210> SEQ ID NO 3
<211> LENGTH: 6
```

```
<212> TYPE: PRT
<213> ORGANISM: Artificial Sequence
<220> FEATURE:
<223> OTHER INFORMATION: Partial peptide sequence.
<220> FEATURE:
<221> NAME/KEY: MISC_FEATURE
<222> LOCATION: (1)..(1)
<223> OTHER INFORMATION: "Xaa" is any amino acid other than Methionine
      and is 5 to 6 amino acids in length.
<220> FEATURE:
<221> NAME/KEY: MISC_FEATURE
<222> LOCATION: (3)..(3)
<223> OTHER INFORMATION: "Xaa" is defined as any amino acid other than
      Methionine.
<220> FEATURE:
<221> NAME/KEY: MISC_FEATURE
<222> LOCATION: (5)..(5)
<223> OTHER INFORMATION: "Xaa" is defined as any amino acid other than
      Methionine and is of unknown length.

<400> SEQUENCE: 3

Xaa Glu Xaa Ser Xaa Lys
1               5

<210> SEQ ID NO 4
<211> LENGTH: 19
<212> TYPE: PRT
<213> ORGANISM: Homo sapiens

<400> SEQUENCE: 4

Ser Leu Ala Phe Glu Glu Gly Ser Gln Ser Thr Thr Ile Ser Ser Leu
1               5                   10                  15

Ser Glu Lys

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 5

Ser Leu Ala Phe Glu Glu Gly Ser Gln Ser Thr Thr Ile Ser Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide.

<400> SEQUENCE: 6

Ser Leu Ala Phe Glu Glu Gly Ser Pro Gln Ser Thr Thr Ile Ser Ser
1               5                   10                  15
```